United States Patent [19]
Dower et al.

[11] Patent Number: 5,958,703
[45] Date of Patent: Sep. 28, 1999

[54] USE OF MODIFIED TETHERS IN SCREENING COMPOUND LIBRARIES

[75] Inventors: William J. Dower, Menlo Park; Gregory L. Heinkel, San Jose; Larry Mattheakis, Cupertino; Peter J. Schatz, Mountain View, all of Calif.

[73] Assignee: Glaxo Group Limited, Greenford, United Kingdom

[21] Appl. No.: 08/758,307

[22] Filed: Dec. 3, 1996

[51] Int. Cl.⁶ ................................................. G01N 33/53
[52] U.S. Cl. .................................. 435/7.1; 435/5; 435/6; 435/7.2; 435/7.21; 435/7.5; 435/21; 435/23; 435/24; 436/501
[58] Field of Search ........................... 435/5, 6, 7.1, 7.2, 435/7.21, 7.5, 21, 23, 24; 436/501

[56] References Cited

U.S. PATENT DOCUMENTS

| | | |
|---|---|---|
| 4,766,075 | 8/1988 | Goeddel et al. . |
| 5,382,513 | 1/1995 | Lam et al. . |
| 5,401,629 | 3/1995 | Harpold et al. . |
| 5,436,128 | 7/1995 | Harpold et al. . |
| 5,565,324 | 10/1996 | Still et al. . |

FOREIGN PATENT DOCUMENTS

| | | | |
|---|---|---|---|
| 0 516 443 A1 | 12/1992 | European Pat. Off. . | |
| WO 94/19461 | 9/1994 | WIPO . | |
| WO 96/24061 | 8/1996 | WIPO | G01N 33/543 |
| WO 96/30392 | 10/1996 | WIPO | C07K 1/04 |
| WO 97/37220 | 10/1997 | WIPO | G01N 33/53 |

OTHER PUBLICATIONS

Chen et al., J. Biol. Chem. vol. 270, #40, pp. 22398–23401 "The Third Ligand Library for Discovery of Peptide Agonists.", 1995.

Smith et al., J. Biol. Chem., vol. 270, #12, pp. 6440–6449 "Rapid Identification of Highly Active and Selective Substrates for Stromclysin and Matrilysin Using Bactriophage Peptide Display Libraries.", 1995.

Barrett and Goldstein (1985), "A Monoclonal Antibody Specific for a Dynorphin Precursor," Neuropeptides 6:113–120.

Barrett et al. (1992), "Selective Enrichment and Characterization of High Affinity Ligands from Collections of Random Peptides on Filamentous Phage," Anal. Biochem. 204:357–364.

Bazan et al. (1994), "Platelet–activating Factor and Retinoic Acid Synergistically Activate the Inducible Prostaglandin Synthase Gene," Proc. Natl. Acad. Sci. USA 91:5252–5256.

Berke (1995), "The CTL's Kiss of Death," Cell 81:9–12.

Cull et al. (1992), "Screening for Receptor Ligands Using Large Libraries of Peptides Linked to the C terminus of the Iac Repressor," 89:1865–1869.

Gossen and Bujard (1992), "Tight Control of Gene Expression in Mammalian Cells by Tetracycline–responsive Promoters," Proc. Natl. Acad. Sci. USA 89:5547–5551.

Himmler et al. (1993), "Functional Testing of Human Dopamine $D_1$ and $D_5$ Receptors Expressed in Stable cAMP–responsive Luciferase Reporter Cell lines," J. Receptor Res. 13(1–4):79–94.

Kinsella et al. (1991), "Molecular Cloning and Characterization of a Candida Tsukubaensis α–Glucosidase Gene in the Yeast Saccharomyces Cerevisiae," Curr. Genet. 20:45–52.

(List continued on next page.)

*Primary Examiner*—Ponnathapura Achutamurthy
*Assistant Examiner*—Joseph W Ricigliano
*Attorney, Agent, or Firm*—Joe Liebeschuetz; Lauren L. Stevens

[57] ABSTRACT

The invention provides methods for screening libraries of complexes for compounds having a desired property, especially, the capacity to agonize, bind to, or antagonize a cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound.

44 Claims, 9 Drawing Sheets

OTHER PUBLICATIONS

Kumar et al. (1992), "Saccharomyces Cerevisiae Cells Secreting an Aspergillus Niger β–galactosidase Grown on Whey Permeate," Biotech. 10:82–85.

Martens et al. (1995), "Peptides Which Bind to E–selectin and Block Neutrophil Adhesion," J. Biol. Chem. 270:21129–21136.

Moreira et al. (1992), "Evaluation of Reporter Genes in Mammalian Cell Lines," Methods in Molecular and Cellular Biology 3:23–29.

Paravicini et al. (1992), "The Osmotic Integrity of the Yeast Cell Requires a Functional PKC1 Gene Product," Mol. Cell Biol. 12:4896–4905.

Price et al. (1995), "Functional Coupling of a Mammalian Somatostatin Receptor to the Yeast Pheromone Response Pathway," Mol. Cell. Biol. 15:6188–6195.

Schatz (1993), "Use of Peptide Libraries to Map the Substrate Specificity of a Peptide–Modifying Enzyme: A 13 Residue Consensus Peptide Specifies Biotinylation in Escherichia coli," Biotech. 11:1138–1143.

Schneider et al. (1996), "An In Vitro Assay of β–Galactosidase from Yeast," BioTechniques 20:960–962.

Vallette et al. (1995), "Unsaturated Fatty Acids Synergistically Enhance Glucocorticoid–induced Gene Expression," Cellular Signalling 7:319–323.

Whitehorn et al. (1995), A Genetic Method for Expression and Use of "Tagged" Soluble Versions of Cell Surface Receptors, Bio/Technology 13:1215–1218.

Wrighton (1991), "Use of Tissue–Plasminogen Activator as a Reporter Gene," Chapter 16 of Methods in Molecular Biology, vol. 7: Gene Transfer and Expression Protocols, E.J. Murray, ed., The Humana Press Inc., C???, NJ, pp. 209–215.

Yamauchi et al. (1993), "Phosphatidylinositol 3–Kinase Functions Upstream of Ras and Raf in Mediating Insulin Stimulation of c–fos Transcription," J. Biol. Chem. 268:14597–14600.

Zaworksi and Gill (1990), Use of Saccharomyces cerevisiae Expressing β–Galactosidase to Screen for Antimycotic Agents ??? Against Yeast Cell Wall Biosynthesis and Possible Application to Pathogenic Fungi, in Molecular Biology Research, Upjohn Company, Kalamazoo, Michigan, 34:660–662.

Zuckermann et al. (1994), "Discovery of Nanomolar Ligands for 7–Transmembrane G–Protein Coupled Receptors from a Diverse N–(Substituted)glycine Peptoid Library," J. Med. Chem. 37:2678–2685.

Normie (1996), "System Uses Photonics for Early Tumor Detection," Biophotonics News, Sep./Oct., pp. 24–25.

Pharmacia Biotech Product Report, "Instructions Cytodex®1, Cytodex 2, Cytodex 3.".

Clontech Product Report, "Reporter Assays & Vectors 26," pp. 161–164.

Tropix Product Report, "Phospha–Light™.".

Corning Product Report, "Fotoform®: a material and a capability.".

Miller (1972), "Experiment 33, Penicllin and Ampicillin Treatment for the Isolation of Auxotrophic Mutants," in Experiments in Molecular Genetics, Cold Spring Harbor Laboratory 33:230–234.

1) Compound released.
2) Compound binds (agonize).
3) Signal Transduction.
4) Transducer molecule interacts with DNA.
5) Reporter gene expressed.
6) Gene product is exported.

Transducing compound bearing complex with modified tether.

Non-transducing compound bearing complex without modified tether.

Separate modified tether complexes from non-modified complexes

Sorted - Transducing compound bearing complex with modified tether.
↓
decoded modified complexes

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Tyr Gly Gly Phe Leu Gly Gly Gly Ser Lys
1               5                   10

(2) INFORMATION FOR SEQ ID NO:2:

(i) SEQUENCE CHARACTERISTICS:
      (A) LENGTH: 48 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Cys Leu Glu Pro Tyr Thr Ala Cys Asp Leu Ala Pro Pro Ala Gly Thr
1               5                   10                  15

Thr Asp Ala Ala His Pro Gly Arg Ser Val Val Pro Ala Leu Leu Pro
                20                  25                  30

Leu Leu Ala Gly Thr Ile Leu Leu Leu Glu Thr Ala Thr Ala Pro
            35                  40                  45

USE OF MODIFIED TETHERS IN SCREENING COMPOUND LIBRARIES

TECHNICAL FIELD

The invention applies the technical fields of combinatorial chemistry and molecular genetics to the identification of compounds with desired properties, such as capacity to bind to, agonize or antagonize a cellular receptor.

BACKGROUND OF THE INVENTION

Several methods have been reported for producing and screening large libraries to identify compounds having specific affinity for a target. These methods include the phage-display method in which randomized peptides are displayed from phage and screened by affinity chromatography to an immobilized receptor. See, e.g., Dower et al., WO 91/17271; McCafferty et al., WO 92/01047; Ladner, U.S. Pat. No. 5,223,409 (incorporated by reference in their entirety for all purposes). In another approach, combinatorial libraries of polymers immobilized on a chip are synthesized using photolithography. See, e.g., U.S. Pat. No. 5,143,854; WO 90/15070 and WO 92/10092. The immobilized polymers are contacted with a labelled receptor and scanned for label to identify polymers binding to the receptor.

A general, and particularly useful, method for synthesizing and screening large libraries of compounds is the encoded synthetic library method (ESL) of Dower et al. In this method, the different compounds in the library are usually synthesized attached to separate supports (e.g., beads) by stepwise addition of the various components of the compounds in several rounds of coupling. A round of coupling can be performed by apportioning the supports between different reaction vessels and adding a different component to the supports in the different reaction vessels. The particular component added in a reaction vessel can be recorded by the addition of a tag component to the support at a second site. After each round of synthesis, supports from the same reaction vessel can be apportioned between different reaction vessels and/or pooled with supports from another reaction vessel in the next round of synthesis. In any, and usually in all rounds of synthesis, the component added to the support can be recorded by addition of a further tag component at a second site of the support. After several rounds of synthesis, a large library of different compounds is produced in which the identities of compounds are encoded in tags attached to the respective supports bearing the compounds. The library can be screened for binding to a target. Supports bearing compounds having a specific affinity for the target are isolated, and the identity of such compounds can be determined by decoding the tags.

All of the above methods have proved successful in isolating compounds having specific affinity for a target of interest. For example, the methods have been used to isolate compounds that bind to a cellular receptor for use as antagonists of receptor-ligand interactions. However, the repertoire of compounds that can be identified by some of the above methods is somewhat limited by the fact that compounds are screened in a tethered format. Furthermore, existing screening methods generally have not been used to distinguish between compounds that merely bind to a receptor, and compounds that are capable of transducing a biological signal through the receptor. The latter compounds are expected to have particularly useful properties, such as the capacity to agonize normal ligand-receptor interactions. These properties can be exploited in many applications such as stimulation of cell or tissue growth, and enzyme, growth factor or hormone replacement therapy.

The present invention provides methods for screening compounds for capacity to transduce a signal through a cellular receptor, thereby allowing the isolation of novel pharmaceuticals.

SUMMARY OF THE INVENTION

The invention provides methods for screening libraries of compounds for a desired activity. In many of the methods, a library of complexes is produced in which each complex comprises a compound under test, a tag recording at least one step in the synthesis of the compound, and a tether susceptible to modification by a reporter molecule. One or more, but not all, of the complexes have a tether that has been modified by the reporter enzyme, the modification indicating that the one or more complexes bear compound(s) having the desired property. At least one complex having a modified tether is separated from the library by virtue of the modified tether. The tag of the complex having the modified tether is then decoded to identify at least one step in the synthesis of a compound having the desired property.

In one aspect, the invention provides methods of screening compounds for capacity to transduce a signal through a cellular receptor. The methods entail providing a plurality of complexes, each complex comprising a compound under test, a tag recording at least one step in synthesis of the compound, and a tether susceptible to modification by a reporter molecule. The complexes are contacted with cells having a receptor and a DNA segment encoding the reporter molecule. At least one compound transduces a signal through the receptor of a cell causing release of reporter molecule expressed from the DNA segment from the cell. The complex having the modified tether is then isolated. The tag of this complex identifies at least one step in the synthesis of the compound transducing the signal.

Optionally, complexes comprise compounds linked to supports by a photocleavable linker and the compounds are freed from the supports by exposure to radiation to allow free compounds to diffuse into contact with cellular receptors. Examples of compounds that can be screened include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. One class of receptor of interest for screening compounds for transducing activity are G-protein coupled receptors. Often, compounds are contacted with supports in a medium that limits diffusion of released reporter, such as a gel matrix. The selection of tether and reporter molecule are interdependent; for example, in one format, the reporter molecule is a protease and the tether bears a site for the protease. In a variation, a second reporter molecule is induced by signal transduction, and the second reporter molecule modifies or induces the reporter molecule which modifies the tether.

In a further variation, the cells further comprise a second DNA segment encoding a site-specific recombinase, and the DNA segment contains a gene encoding the reporter molecule, which gene is disrupted by an inactivating sequence flanked by sites recognized by the site-specific recombinase. The transducing compound causes expression of the site-specific recombinase, which excises the inactivating sequence from the gene resulting in expression of the reporter molecule, which is released from the cell and modifies the tether of the complex from which the compound was released.

In a second aspect, the invention provides additional methods for screening compounds for capacity to transduce a signal through a cellular receptor. In these methods, a plurality of supports are provided, each support bearing a compound under test, and a tether susceptible to modification by a reporter molecule, however, the supports need not have tags. The supports are contacted with cells having a receptor and a DNA segment encoding the reporter molecule. The compounds are partially freed from the supports, whereby at least one compound transduces a signal through the receptor of a cell causing expression of the reporter molecule, which reporter molecule is released from the cell and modifies the tether of the support from which the compound transducing the signal was partially freed. The support having the modified tether is isolated, which support bears the compound transducing the signal.

In another aspect, the invention provides a further method for screening compounds for capacity to transduce a signal through a cellular receptor. In these methods, compounds are provided as an array on a membrane. The membrane is contacted with cells having a receptor and a DNA segment encoding a reporter molecule. At least one compound transduces a signal through the receptor of a cell causing expression of the reporter molecule, which reporter molecule is released from the cell and modifies the membrane at a position proximate to the compound transducing the signal. The modification allows the compound transducing the signal to be isolated. The array of compounds can be provided as an array of cells, each producing a compound under test. For example, the compounds may be secondary metabolites.

In another aspect, the invention provides still further methods of screening compounds for capacity to transduce a signal through a cellular receptor. The methods entail providing a collection of cells, each secreting a compound under test and each bearing a tether on its surface. The collection of cells is contacted with reporter cells having a receptor and a DNA segment encoding a reporter molecule; whereby at least one compound transduces a signal through the receptor of a reporter cell causing expression of the reporter molecule, which reporter molecule is released from the reporter cell and modifies the tether of the cell from the collection of cells secreting the compound that transduced the signal. The cell having the modified tether is isolated, wherein the compound transducing the signal is isolated by culturing the cell.

In another aspect, the invention provides methods of screening compounds for capacity to inhibit enzymatic modification of a substrate. The methods comprise providing a plurality of complexes, each complex comprising a compound under test, a tag recording at least one step in synthesis of the compound, and a tether susceptible to modification by an enzyme. The complexes are contacted with the enzyme and the compounds are released from the complexes within a matrix that retains a released compound in proximity to the complex from which it was released, whereby the enzyme modifies the tether of complexes from which compounds lacking enzyme inhibiting activity were released without modifying the tether of at least one complex from which a compound having enzyme inhibiting activity was released due to protection of the tether by the compound. At least one complex is isolated having the unmodified tether, wherein the tag of the complex identifies at least one step in the synthesis of the compound with inhibiting activity.

The invention further provides methods of screening compounds for capacity to bind to a receptor. The methods comprise providing a plurality of first complexes, each first complex comprising a compound under test, a tag recording at least one step in synthesis of the compound, and a tether susceptible to modification by a reporter molecule. The first complexes are then contacted with second complexes comprising a ligand specifically bound to the receptor, whereby either the ligand or receptor is immobilized to a support and the other is linked to a reporter molecule, whereby at least one compound competitively dissociates the ligand and the receptor, thereby allowing the linked reporter molecule to modify the tether of the first complex comprising the compound that competitively dissociates the ligand and the receptor. The first complex having the modified tether is then isolated. The tag of the complex identifies at least one step in the synthesis of the compound that competitively dissociates the ligand and the receptor.

In another aspect, the invention provides methods of screening compounds for capacity to antagonize a ligand of a cellular receptor. The methods comprise providing a plurality of complexes, each complex comprising a compound under test, a tag recording at least one step in synthesis of the compound, and a tether susceptible to modification by a reporter molecule. The complexes are contacted with cells and the ligand, wherein the cells have a receptor, a first DNA segment encoding the reporter molecule and a second DNA segment encoding a lethal gene whose expression is induced when the ligand binds to the receptor. In cells proximate to a complex bearing a compound that is an antagonist, the antagonist blocks signal transduction by the ligand through the receptor, the reporter molecule is expressed and released from the cell, where it modifies the tether of the complex from which the compound was released. In cells proximate to complexes bearing compounds that are not antagonists, the ligand transduces a signal through the receptor of a cell causing expression of the lethal gene, the cells die, and the tethers of the complexes bearing compounds that are not antagonists remain unmodified. The complex having the modified tether is isolated. The tag of the complex identifies at least one step in the synthesis of the compound transducing the signal.

BRIEF DESCRIPTION OF THE FIGURES

FIG. 1B shows a transducing compound binding to a cellular receptor and transducing a signal resulting in expression of a reporter gene and export of a reporter molecule from the cell. The lower part of FIG. 1C shows the reporter molecule modifying the tether of complex from which the compound transducing the signal was released. The upper part of FIG. 1C shows that the tethers of complexes lacking transducing compounds remain unmodified. FIG. 1D shows complexes bearing modified tethers are being separated from complexes bearing unmodified tethers. Tags of complexes bearing modified tethers can then be decoded to reveal the identity of transducing compounds.

FIG. 2A shows cleavage of the tether by a protease, such as tPA, to release an epitope whereas the tether loses capacity to bind a target. FIG. 2B shows cleavage of the tether to produce a free end required for target binding.

FIG. 3A shows tether modified by biotin. FIG. 3B shows tether modified to acquire binding site for an antibody.

DEFINITIONS

A DNA segment is operably linked when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

A library member is isolated from a library if it exists in substantially enriched form in a subpopulation of the library. Library members having desired activity are usually further isolated to homogeneity.

DETAILED DESCRIPTION

I. Methods of Screening Encoded Libraries

Figure 1A:
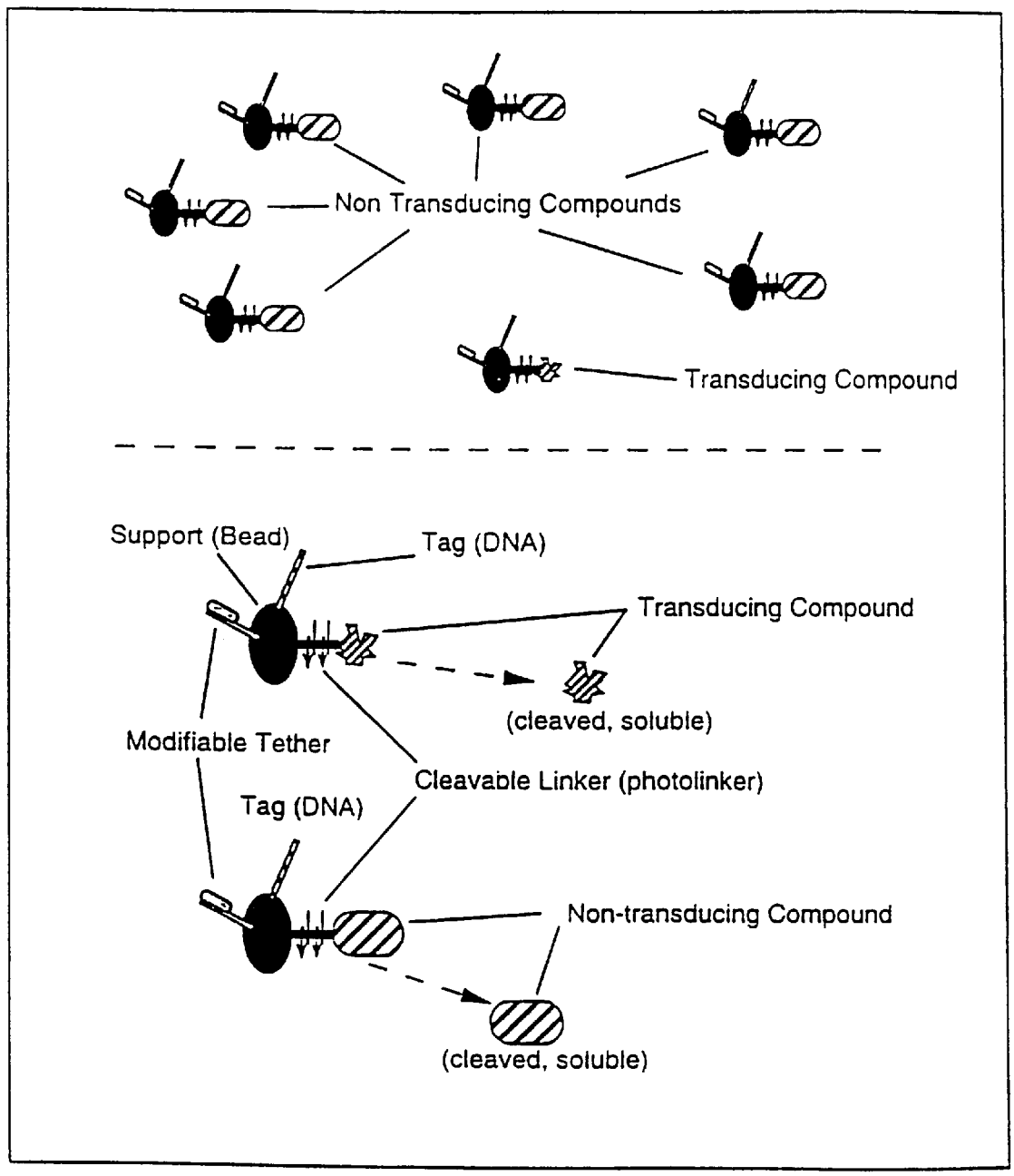
FIG. 1A through FIG. 1D: Scheme for screening a library of complexes bearing compounds, tags and tethers for compounds having transducing activity. The upper panel of FIG. 1A shows a library of complexes. Most complexes bear nontransducing compounds. The lower panel of FIG. 1A shows cleavage of compounds from the complexes. Both transducing and nontransducing compounds are cleaved.
Figure 1B:
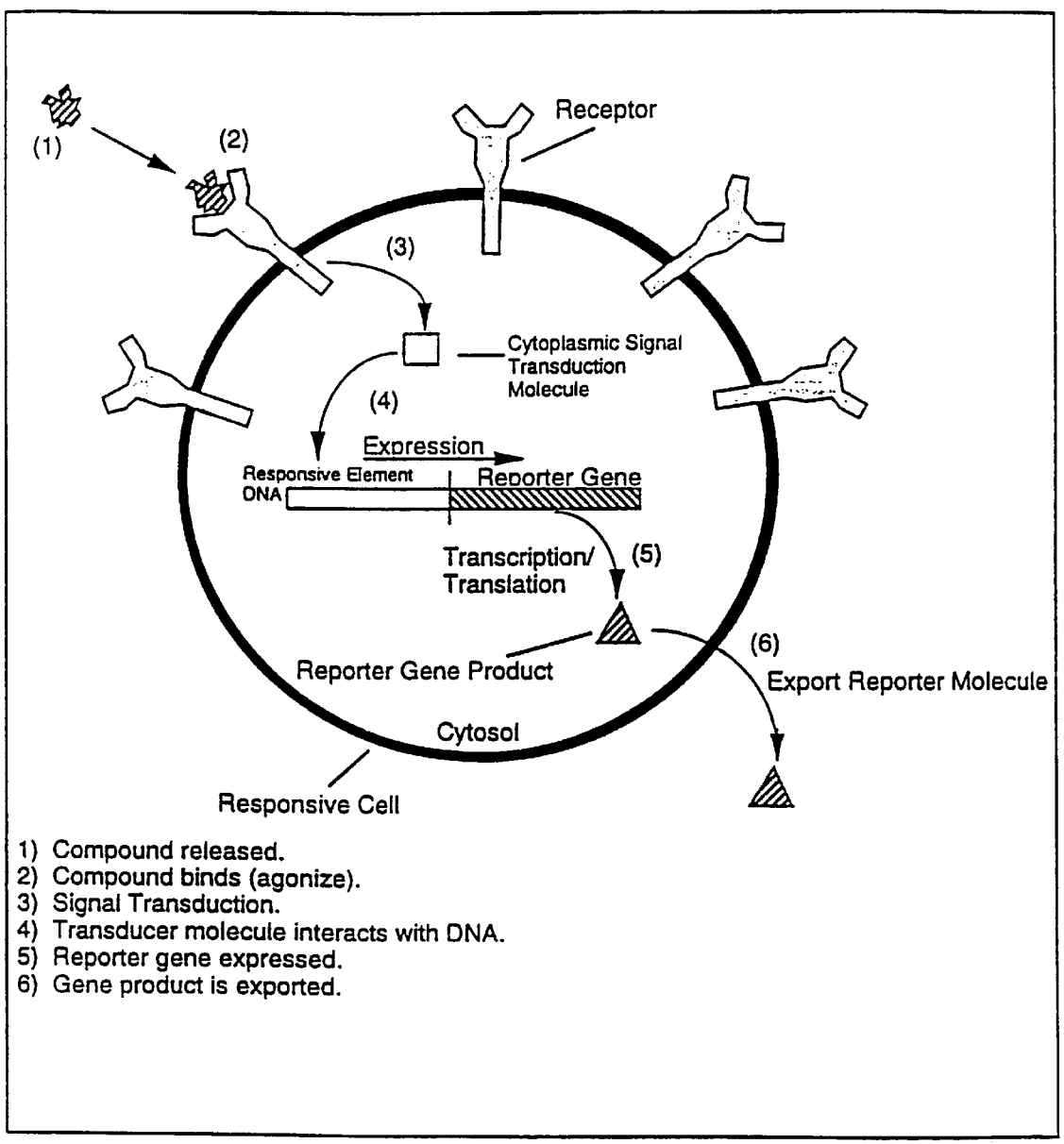

The invention provides methods for screening libraries of different compounds to identify particular compounds capable of transducing a signal through a biological receptor. The general principles of some of these methods are exemplified by the scheme shown in FIG. 1A through FIG 1D. FIG. 1A illustrates a library of compounds to be screened. In this example, the library members are complexes comprising a support with three entities attached, a compound to be screened, a tag (which serves to identify the compound or components thereof), and a tether. Such a library is similar to the ESL libraries described by Dower et al., supra except for the tether in the present libraries. FIG. 1B shows the type of cell used in screening the libraries (i.e., a reporter cell). A reporter cell has a receptor and a reporter construct capable of being expressed when the receptor is stimulated.

Figure 1C:
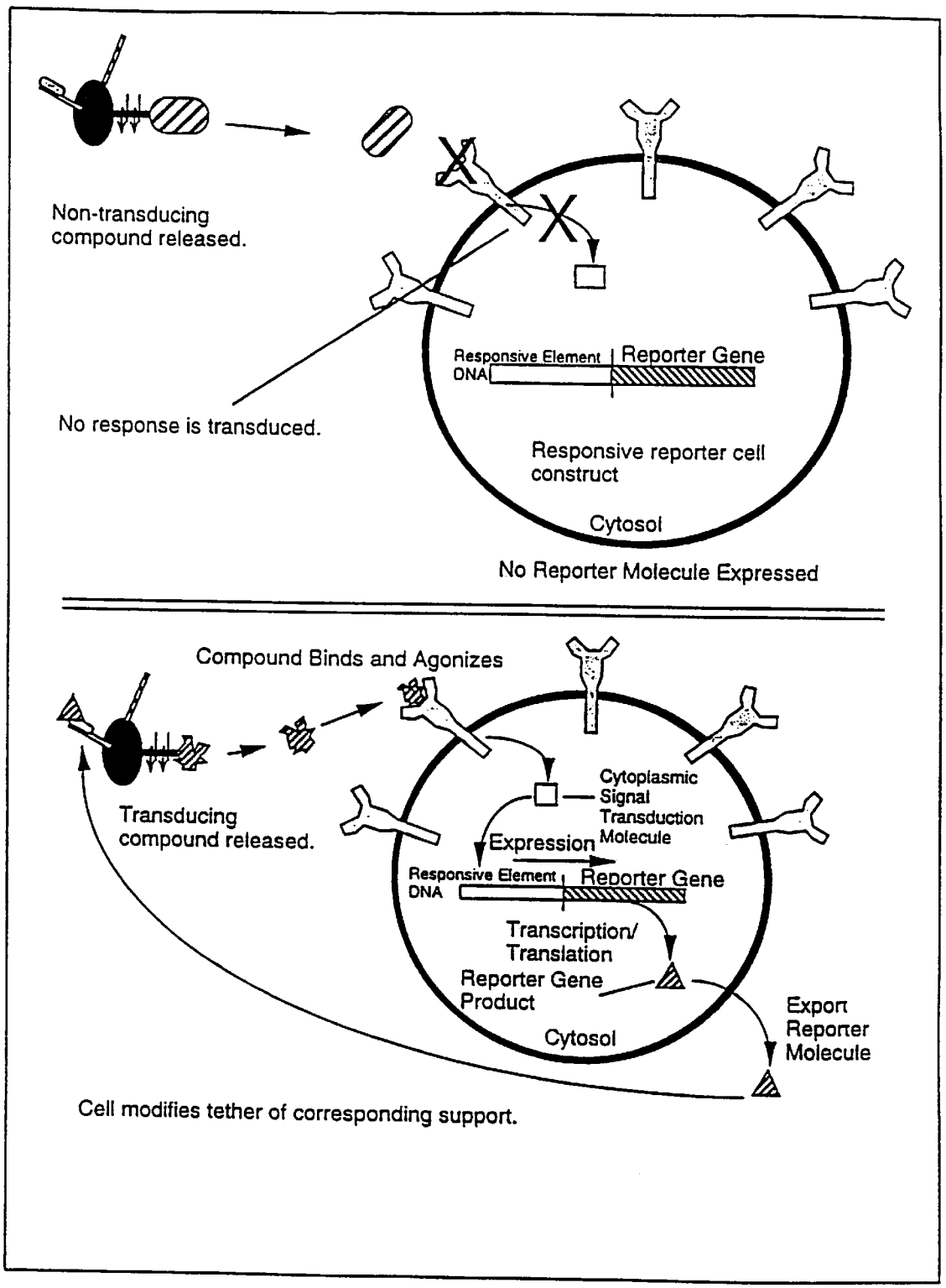

FIG. 1C shows the complexes in the library being contacted with reporter cells. After mixing of complexes and reporter cells, the compounds being screened are usually cleaved from their respective complexes. After cleavage, the compounds diffuse into contact with the cellular receptors. Some of the compounds are able to transduce a signal through a receptor, thereby inducing transcription and expression of the reporter construct to produce a reporter molecule, as shown in the upper half of the panel. The reporter molecule is secreted or otherwise released from the cell, where it comes into contact with the complex from which the compound transducing the signal was released. The reporter molecule then modifies the tether of this complex. Thus, after this series of events, the complex which originally bore a transducing compound appears as shown at the left side of FIG. 1D. The complex now has a tag, what remains of the linker following cleavage of the compound being screened from the complex, and a modified tether.

Figure 1D:
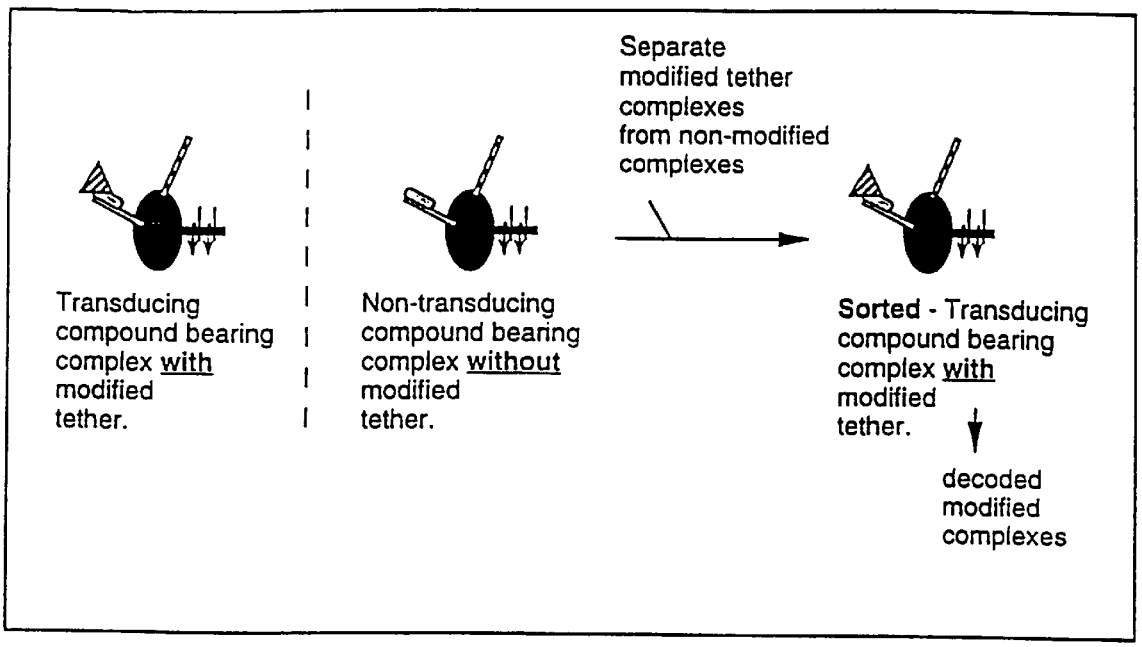

Nontransducing compounds do not cause reporter molecules to be released from adjacent report cells (see lower half of FIG. 1C). Thus, the respective complexes from which such compounds derived appear as shown in the right of FIG. 1D. The complexes have a tag, what remains of the linker following cleavage of the compound to be screened, and an unmodified tether.

Supports having modified tethers are separated from supports having unmodified tethers. Although it is known that the supports having modified tethers once bore transducing compounds, these compounds are no longer attached. Nevertheless, the identity of these compound can be determined by decoding the tags attached to the supports. Compounds having capacity to transduce a signal can then be resynthesized based on the information from the tags.

A. Library Construction (1) ESL Libraries

The construction of encoded synthetic libraries (ESL) has been described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes) and summarized in the Background Section above. The ESL method for synthesizing compounds typically involves a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. The monomer set can be expanded or contracted from step to step; or the monomer set could be changed completely for the next step (e.g., amino acids in one step, nucleosides in another step, carbohydrates in another step). A monomer unit for peptide synthesis, for example, can include single amino acids or larger peptide units, or both. The size of libraries generated by such methods can vary from 2 different compounds to $10^2$ $10^4$, $10^6$, $10^8$, $10^{10}$, $10^{12}$ or $10^{15}$.

Supports can be of any shape, although they are often roughly spherical. The supports need not necessarily be homogenous in size, shape, or composition; although the supports usually are uniform. The supports can be a single particle, or two or more linked particles. The latter arrangement allows the segregation of molecules or oligomers and identifier tags into discrete "zones" and permits the use of widely different chemically reactive groups and chemistries for attachment. Optionally, libraries can be formed without solid supports in which compounds are joined to tags via linkers.

Supports can consist of many materials, limited primarily by capacity for derivatization to attach any of a number of chemically reactive groups and compatibility with the chemistry of oligomer or other molecular synthesis and tag and tether attachment. Suitable support materials include solids such as glass, latex, heavily cross-linked polystyrene or similar polymers, gold or other colloidal metal particles. Such solid supports are derivatized with chemical groups typical for solid state synthesis of the intended compounds. In general, the solid support size is in the range of 1 nm to 100 μm, but a more massive solid support of up to 1 mm in size may sometimes be used. Monobeads™ (10 µm) (Pharmacia Fine Chemicals AB, Uppsala Sweden) or their equivalent, are particularly useful as solid supports.

Compounds screenable by the present methods include, for example, peptides, oligonucleotides, oligo N-substituted glycines, and polycarbamates. Other compounds include polymers formed from one or more of the following monomer types: amino acids, carbamates, sulfones, sulfoxides, nucleosides, carbohydrates, ureas, phosphonates, lipids, esters. Other compounds that can be synthesized in a component-by-component fashion can also be screened including benzodiazepines, hydantoins, and peptidylphosphonates (see U.S. Ser. No. 08/119,700,filed Sept. 9, 1993, and U.S. Pat. No. 5,339,115, each of which is incorporated herein by reference).

The identifier tags identify reaction steps that an individual compound has experienced. For syntheses proceeding to high yield and effectively generating single products (e.g., peptide and oligonucleotide synthesis), the tag explicitly specifies one, and usually all, of the components of the product, and the resulting product structure. In some situations, for example, when only a small number of monomer units of an oligomer are varied, one may need to identify only those monomers which vary among the oligomers. For other syntheses giving variable yields and frequently multiple products (such as regio- and stereoisomeric structures), a mixture of compounds is sometimes obtained on each support. In this situation, the tag may not uniquely specify the chemical structure of an associated entity. Rather, the tag encodes the synthetic protocol (e.g., reagents and reaction conditions) by which a member of the library was constructed. The library is screened to identify "active recipes" that then can be reproduced on a preparative scale and fractionated (if necessary) to isolate the bioactive component(s).

The tags can be attached immediately before, during, or after a round of monomer addition to compounds or other reaction, as compatible with the type of identifier tag, modes of attachment, and chemistry of oligomer or other molecular synthesis. The code can be contained in a single polymeric sequence of individual tags or can be embodied by the presence or absence of individual different tags on the support.

The identifier tag has a recognizable feature that is, for example, microscopically or otherwise distinguishable in shape, size, mass, charge, or emissions. This recognizable feature may arise from the spectral, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library (i.e., the sequence of monomers of any oligomer) by reading the identifier tag.

One can construct microscopically identifiable tags as small beads of recognizably different sizes, shapes, or colors, or labeled with bar codes. The tags can be machine-readable luminescent or radioactive labels. The identifier tag can also be an encodable molecular structure. The information may be encoded in the size (the length of a polymer) or the composition of the molecule.

Oligodeoxyribonucleotides are one form of information-bearing identifier tags. Oligonucleotides are a natural, high density information storage medium. The identity of monomer type and the step of addition or any other information relevant to a chemical synthesis procedure is easily encoded in a short oligonucleotide sequence. Oligonucleotides, in turn, are readily amenable for attachment to a wide variety of solid supports, oligomers, linkers, and other molecules. To facilitate oligonucleotide tag identification, one has a variety of options. For instance, one can read the tag directly from the bead by sequencing or hybridization. One can also amplify oligonucleotide tags to facilitate tag identification, e.g., by PCR.

Inert hydrocarbon tagging molecules, which are discretely resolvable by a variety of methods, such as chromatography, can also be used. See Ohlmeyer et al., *Proc. Natl. Acad. Sci. USA* 90, 10922–26 (December 1993), and WO 94/08051, each of which is incorporated herein by reference for all purposes. Such tags can encrypt a binary code to each chemical building block.

Most steps of the ESL methods described above can be incorporated without modification to generate libraries suitable for screening by the present methods. However, some features of the libraries used in the present methods require further comment. Most importantly, members of some of the present libraries have an additional component to the tag and compound of previous libraries, that is, a tether. A tether is any molecule that is modified by a reporter molecule in a manner such that complexes bearing modified tethers can be distinguished from complexes bearing unmodified tethers by virtue of the modification. The choices of tether and reporter molecule are interdependent.

Usually, a tether is linked to a support, which also bears a compound being screened and a tag. However, in some instances, the tether is an integral part of the support, and the reporter molecule binds specifically or nonspecifically to the support. In many applications, the tether is a polypeptide. Because, in general, all supports bear the same tether, its attachment presents no particular difficulty. The tether can be attached either before, after, or contemporaneous with the addition of the other components. Usually, the tether is preformed before attachment (as distinct from being synthesized in a step-by-step manner). The tether is generally attached to a separate site on the support from either the tag or the compound being screened. If the tether is attached before the compound and tag, the sites at which addition of the latter two compounds are to be added can be protected during tether addition and deprotected thereafter.

Usually, the compounds to be screened are connected to the support with a cleavable linker. Preferred photocleavable linkers are 6-nitroveratryloxycarbonyl (NVOC) and other NVOC related linker compounds (see WO 90/15070 and WO 92/10092; U.S. Ser. No. 07/971,181, filed Nov. 2, 1992). Other suitable linkers include nucleic acids with one or more restriction sites, or peptides with protease cleavage sites (see, e.g., U.S. Pat. No. 5,382,513). The tether and the tag can also be connected to the support or each other via linkers, but any such linkers should not be cleavable under the conditions in which the linker joining the compounds to the supports is cleavable.

(2) Other Encoded Libraries

Libraries of compounds suitable for screening by the present methods can also be generated by other methods such as phage display. In these methods, different peptides to be screened are displayed from one coat protein of a phage and the tether, which is the same in each phage, is displayed from another coat protein. For example, the peptides to be screened can be displayed from gIII and the tether from gVIII of a filamentous phage, or vice versa. Accordingly, in the terminology of encoded libraries, the phage particle is the support and the portion of the phage genome encoding the peptides to be screened is the tag.

Peptides and tethers can also be displayed from genetic entities, such as bacteria, plasmids, polysomes or spores.

B. Cells and Reporter Systems

The cells used for analysis of signal transduction should be capable of expressing the receptor of interest in functional form such that the receptor can transduce a signal to induce expression of a reporter molecule from a reporter construct. The cell types typically used in genetic engineering such as E. coli, yeast, insect cells, amphibian or mammalian cell lines are suitable. Yeast expressing a seven transmembrane mammalian receptor is described by Price et al., Mol. Cell. Biol. 19, 6188–6195 (1995). Suitable mammalian cell lines include CHO, COS, HeLa, and 3T3. Primary cultures of natural cells (e.g., hemopoietic cells) expressing receptors of interest can also be used provided the cells naturally have, or can be transfected with, an appropriate reporter construct.

The term receptor is used broadly to refer to a cellular macromolecule, which interacts with a compound, and transduces a signal as a result of such interaction that causes, directly, or indirectly a detectable change in the transcription or translation of a gene or localization of a gene product. The compound may transduce a signal alone or may act in conjunction with another ligand. Often the signal is transmitted between the receptor and the gene by a cascade of intracellular events.

Many receptors are cell surface proteins, which have one or more of each of the following domains: an extracellular domain to interact with a compound, a transmembrane domain and an intracellular domain, which transduce a signal, directly or indirectly to a gene. Such receptors include ion channels (e.g., calcium, sodium, potassium channels), growth factor receptors, muscarinic receptors, acetylcholine receptors, GABA receptors, glutamate receptors, adrenergic receptors, dopamine receptors (see Harpold, U.S. Pat. No. 5,401,629 and U.S. Pat. No. 5,436,128), and adhesion proteins such as integrins, selecting, and immunoglobulin superfamily members (see Springer, Nature 346, 425–433 (1990). Osborn, Cell 62, 3 (1990); Hynes, Cell 69, 11 (1992)). Often the receptor is heterologous to the cell used for screening, in which case the receptor is expressed from a recombinant construct introduced into the cell.

Some growth factor receptors, such as fibroblast growth factor receptor, have tyrosine kinase activity. When such a growth factor receptor binds to its growth factor or an analog, the tyrosine kinase activity phosphorylates an intracellular protein, thereby changing the activity of the protein in some manner. The modified protein, then directly or through further intermediates, induces or inhibits transcription of a gene (e.g., birA or tissue plasminogen activator). Other receptors include NGF and VEGF. Cytokine receptors are also of interest.

Other receptors are referred to as G-protein receptors and include substance K receptor, the angiotensin receptor, the α- and β-adrenergic receptors, the serotonin receptors, and PAF receptor. See, e.g., Gilman, Ann. Rev. Biochem. 56, 625–649 (1987). These receptors usually have seven transmembrane segments connected by alternating intra and extracellular domains. Binding of a ligand or analog to a G-protein receptor induces an alteration in receptor G-protein interaction. The receptor G-protein interaction releases GDP specifically bound to the G protein and permits the binding of GTP, which activates the G protein. Activated G-protein dissociates from the receptor and activates an effector protein, which in turn regulates intracellular levels of second messengers, such as adenyl cyclase, guanyl cyclase, and phospholipase C.

Some receptors are intracellular proteins, such as enzymes, nuclear receptors (e.g., FXR (Farnesoid X Receptor), PPARb (Peroxisome Proliferator Activator Receptor Delta), and RZR (Retinoid Z Receptor)), organelle receptors, and hormones. If the receptor under test is an intracellular protein, the cell type chosen should have the inherent or engineered capacity to take up the compounds of the kind being tested.

Figure 2A:
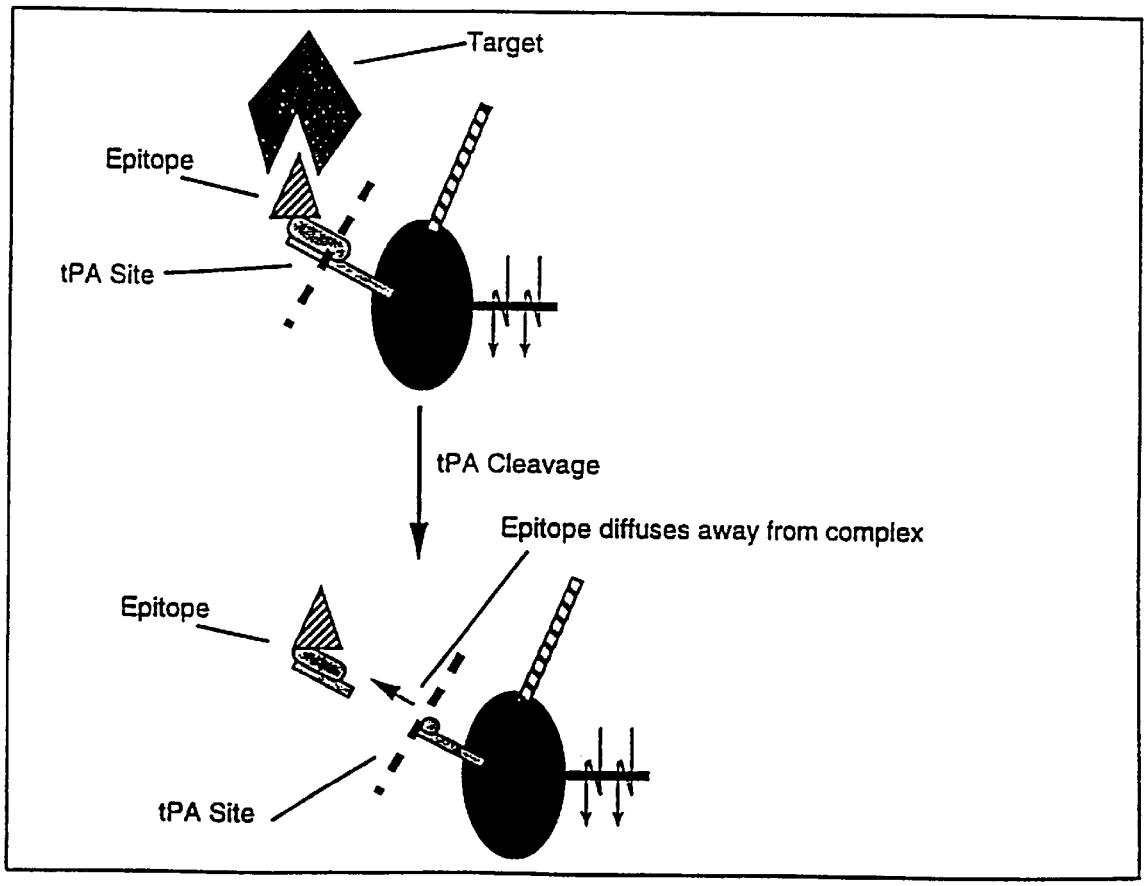
FIG. 2A and FIG. 2B: Schemes for modification of a tether that allow separation of modified and unmodified tethers.
Figure 2B:
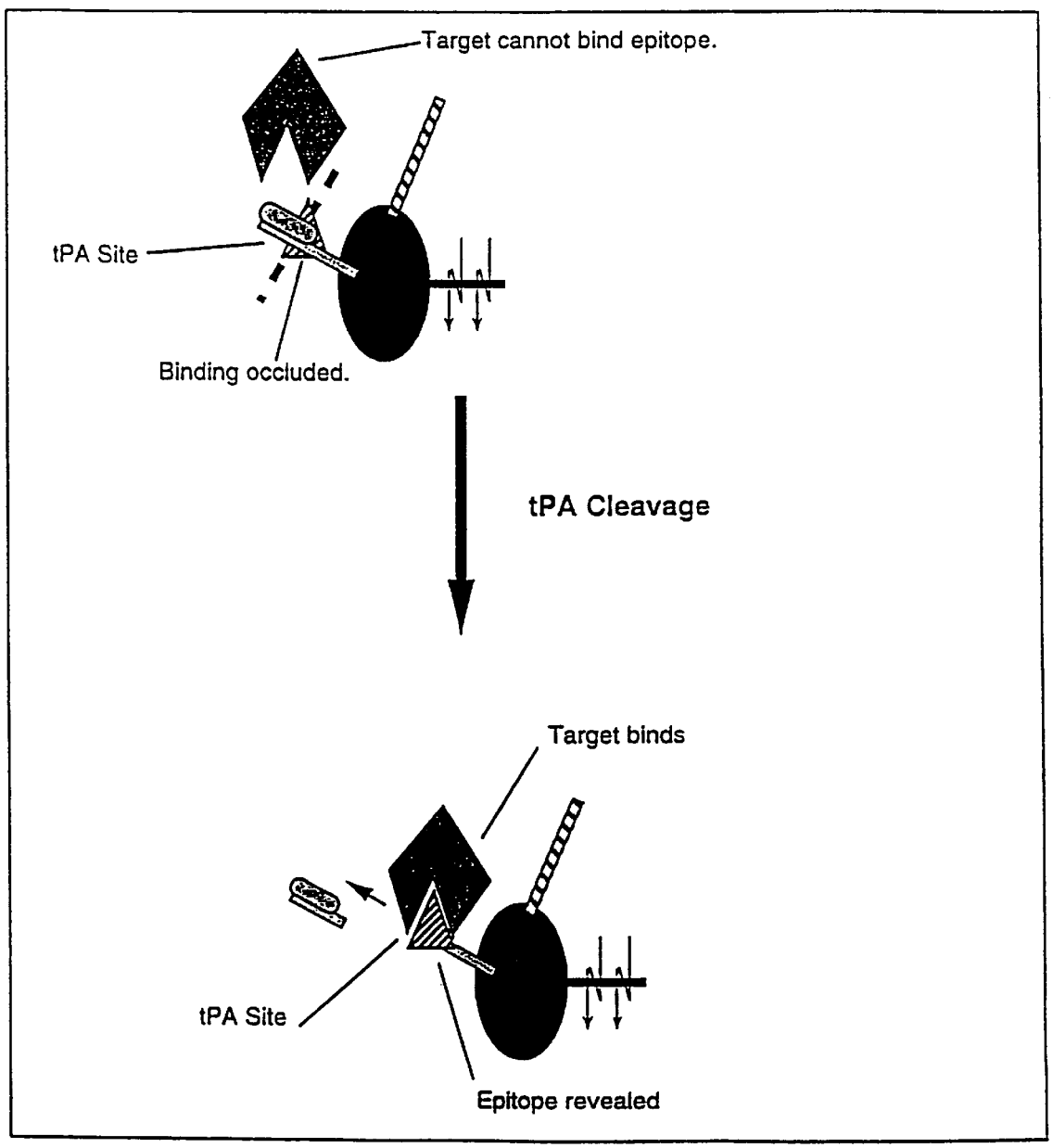

A reporter gene is any gene that produces an easily detectable gene product, which can be RNA or protein. The reporter gene can be naturally present in the reporter cell but is usually an exogenous gene transfected into the cell. The gene product should be capable of being expressed in the cell-type chosen and should be capable of directly or indirectly modifying the tether attached to supports bearing the compounds. Suitable reporter molecules include lytic enzymes, such as proteases, nucleases, lipases, phosphatases, sugar hydrolases, and esterases. Such enzymes cleave a tether bearing a cleavage site recognized by the enzyme. For example, if the reporter molecule is the protease tPA (see Goeddel et al., U.S. Pat. No. 4,766,075), the tether can be a substrate containing a tPA cleavage site such as one of the substrates described by Ding et al., PNAS 92, 7627–31 (1995). At one terminus of this substrate peptide is attached an epitope or other molecule having affinity for a known target. For example, an epitope to any available antibody, or biotin can be used. Many high affinity hexapeptide ligands are known for the anti-dynorphin mAb 32.39, for example Barrett et al., Neuropeptides 6, 113–120 (1985) and Cull et al., PNAS 89, 1865–1869 (1992). The cleavage site and binding site are arranged so that cleavage releases the binding site from the support (see FIG. 2A). Alternatively, cleavage of a site on a tether can create a binding affinity not previously present (see FIG. 2B). For example, some epitopes are recognized by antibodies only when the epitope has a free terminus and not when that terminus is internal to a fusion protein. The MAb 3E7, for example, recognizes such an epitope (see Dower et al., WO 91/17271; Schatz, Biotechnology 11, 1138–43 (1993)).

A variety of nonlytic modifying enzymes can also be used as reporters. For example, tyrosine kinase can phosphorylate a substrate peptide to create an epitope for anti-tyrosine phosphate antibody. Alternatively, the biotinylating enzyme, BirA, can be used to place a biotin on the short artificial peptide substrate described by Schatz, Biotechnology 11, 1138–43 (1993). In either case, the tether is modified to allow its ready separation from unmodified tethers. Other reporter molecules are binding proteins that recognize a hapten or epitope on the tether. Some such reporter molecules have a domain recognizable by a secondary reagent. An example of this type of reporter is a soluble extracellular domain of the IL-1 receptor containing at its C-terminus the HPAP epitope. Whitehorn et al., Bio/Technology 13, 1215–1218 (1995). The tether is the IL-1 ligand. Binding of the IL-1 receptor to the tether labels the affected beads with the HPAP epitope carried by the receptor. Other reporter genes that can be used include luciferase (de Whet et al., Mol. Cell. Biol. 7, 725–737 (1987)), chloramphenicol acetyl transferase, β-galactosidase (e.g., Kumar et al., Bio/Technology 10, 82–85 (1992)) and alkaline phosphatase (Toh et al., Eur. J. Biochem. 182, 231–238 (1989)). These reporter genes process a chemical substrate on the tether to a product having a characteristic spectral emission not present in unmodified tethers. For example, β-galacotosidase processes X-gal to generate a blue color.

Other suitable reporter molecules are bifunctional molecules capable of binding to a tether at one end and a label at the other end. For example, an IL-1 receptor linked to an epitope of an antibody (e.g., Ab179) at its C-terminus can bind to a tether, such as IL-1 and to the antibody. Thus, complexes become modified by attachment of IL-1 to a tether and modified complexes can be distinguished from unmodified complexes by screening for capacity to bind the antibody.

A preferred reporter gene is secreted alkaline phosphatase (SEAP) (available from Clontech) used in conjunction with a tether comprising biotinylated form of the marker substrate peptide (phospho-YGGFLGGGSK[biotin]) (SEQ ID NO:1). This tether can be attached to beads that have previously been treated with streptavidin, which is passively absorbed by the beads. The phosphorylated peptide is not recognized by antibody 3E7, but once tyrosine is dephosphorylated, the peptide is uncaged and reactive with the antibody. An analogous reporter system employs β-galactosidase as the reporter molecule and gal-YGGFLGGGSK[biotin] (SEQ ID NO:1) as the tether.

The reporter gene is expressed from a construct in which the gene is operably linked to a promoter, and optionally, a DNA sequence encoding a signal sequence, and/or other regulatory sequences such as enhancers, activators and repressors. The promoter is chosen from a gene whose expression is activated by signal transduction through the receptor of interest. The signal sequence, if present, should be recognized by the cell type employed and be capable of directing the secretion of the reporter molecule from the cell. Other regulatory sequences, if present, are often selected from sequences flanking the promoter of the gene from which the promoter is obtained. However, they can also be obtained from other genes, which may or may not be activated by the receptor. For example, the immunoglobulin heavy chain $\mu$ enhancer can be used to stimulate expression of many kinds of heterologous genes. The inclusion of regulatory sequences serves to amplify the transduced signal from the reporter gene and/or reduce background expression in the absence of such signal, thereby increasing the sensitivity of the assay.

As an example, when the receptor is a G-protein linked receptor, the promoter and regulatory sequences linked to a reporter gene can be obtained from the 5'-flanking region of the genes fos or jun. Hill et al., *EMBO J* 14, 5037–47 (1995); Pennymaker et al., *FASEB J*, 8, 475–8 (1994). Fos and jun encode proteins that participate in the regulation of many cellular genes. The 5' flanking sequences of fos and jun genes contain elements responsive to activation by $Ca^{2+}$ and cAMP, both of which are secondary messengers in G-protein linked receptor signal transduction. For example, linkage of the reporter gene to the fos promoter and 700 bp upstream region is suitable.

C. Contacting of Compounds and Reporter Cells

The assay can be performed by placing the library of complexes in proximity to the reporter cells in a matrix that allows diffusion of compounds and reporter molecules over short distances (commensurate with the dimensions of the complexes and cells) but retains the complexes and cells in substantially fixed positions relative to one another. Usually, the cells are present in excess with respect to the complexes (e.g., about 5, 10 or 100-fold excess) to minimize or prevent "cross-talk"—the incidental labeling of a complex not carrying a transducing compound, by virtue of its physical proximity to a complex that does carry a transducing compound.

One suitable format is a suspension of an excess of cells and a controlled concentration of supports in a layer of soft agarose or agar (preferably low melting temperature) several mm thick (a "thick 2-D" arrangement). For example, a library of $10^9$ 10 $\mu$m beads can be screened with $10^{10}$ cells spread as a lawn on a thin soft agar layer on an area the size of a cafeteria tray. Another suitable format is to distribute the supports in an array on a membrane and contact the membrane with a layer of reporter cells. In a variation, supports and cells are distributed in gel microdrops, such that only one or a few supports are present in the same drop.

Alternatively, the assay can be performed in a 3D format by contacting cells and complexes in a column matrix. The column matrix can comprise a plurality of compound bearing supports interspersed among a plurality of cell culture microcarriers (Pharmacia) that have responsive reporter cells adhered on the surface as described by Pharmacia. See *Microcarrier Cell Culture* (Pharmacia, Sweden, 1981). The matrix of supports and microcarriers can further be diluted by the addition of inert solid beads to the matrix contained within the column. The fluid matrix can be maintained or exchanged using similar methods to that of standard column chromatography. In a further 3D format, cells and complexes can be contacted in a liquid medium with relative movement of the two constrained by temporary crosslinking. Suitable heterobifunctional cross-linking agents are described by Pierce, *ImmunoTechnology Catalog and Handbook* (1991), pp. E10–E18. Crosslinking can occur before or after addition of the cells and complexes to the liquid matrix, but is usually complete before release of compounds from the supports. After modification of the tether has occurred, the crosslink between cells and supports is usually broken before performing subsequent steps such as the separation of complexes bearing modified tethers from complexes bearing nonmodified tethers. Supports can be crosslinked to cells or cell-microcarrier complexes by several methods. They can be crosslinked by chemical methods described by Pierce, or preferably they can be crosslinked by simple absorption of the support to the cells, cell/microcarriers or, more preferably, to the microcarrier itself with the cells grown onto the carrier after the support had been linked to it. Often the supports are linked by a high affinity interaction between a support bearing a ligand and a receptor on the cell surface or an antibody or receptor linked to the support binding a ligand display by the cell (see Whitehorn et al., *Bio/technology* 13, 1215–1219 (1995)).

Having contacted the complexes with the reporter cells, compounds are usually freed from the complexes. Freeing the compounds from the complexes speeds the rate of diffusion of compounds to receptors and allows compounds to interact with a receptor without any conformational constraints imposed by the rest of the complex. Freeing compounds is particularly appropriate for libraries having compounds linked to relatively massive supports, such as beads, but is less important in libraries having small biological supports such as phage, or in libraries, in which tag, tether and compound are linked directly to each other without an intervening support. Compounds are usually freed from a complex by cleavage of a linker connecting the compounds to the complex. In the thick 2D and liquid 3D formats noted above, linkers connecting compounds to supports are accessible to photolytic cleavage. Alternatively, the compounds can be connected to the complexes with a linker subject to enzymatic cleavage, and the compounds released by exposure to the enzyme. For example, the enzyme can be included in the soft agarose or other matrix in which cells and complexes are contacted. For coordinated release of the different compounds, the complexes and reporter cells can be contacted at low temperature at which the enzyme is inactive, and the enzyme can then be activated by raising the temperature. An analogous approach can be used to release compounds connected to complexes by linkers susceptible to chemical cleavage.

After contacting the complexes and cells in a suitable medium and releasing the compounds from the complexes, a released compound diffuses to a receptor of a cell proximate to the complex that released the compound. Some compounds transduce a signal through the receptor, whereas others (usually, the vast majority of compounds) do not. If a compound does transduce a signal, the signal induces expression of the reporter molecule within the cell.

Often the reporter molecule is expressed as a fusion protein having a signal sequence, in which case, the signal directs the secretion of the reporter molecule from the cell. Alternatively, the reporter molecule can be expressed without a signal sequence, in which case it accumulates in the cell. After a suitable period of accumulation of reporter molecule, cells are lysed (e.g., by infusion of detergent into the matrix) releasing reporter molecules to the medium proximate to the cell in which they were originally contained. This alternative procedure can be advantageous in coordinating a release of a burst of reporter molecules from a stimulated cell thereby increasing the sensitivity of the assay.

Irrespective whether the reporter molecule is released by secretion or lysis, on leaving the cell, it diffuses a short distance through the surrounding media to the complex from which the compound inducing expression of the reporter was released. The reporter molecule then modifies the tether of the complex in some manner. For example, the reporter molecule can cleave the tether, bind to the tether or enzymatically alter the tether. Thus, complexes are marked (by the modified tether) as carrying a compound that activated a cell.

D. Separating Modified Tethers from Nonmodified Tethers

The next step is to separate, or at least, enrich for complexes bearing modified tethers from the total pool of complexes. The manner of separation or enrichment depends on the nature of the modification. In several of the examples discussed above, the modification either confers or destroys a capacity to bind a specific target. For example, if the modification is enzymatic cleavage, the modification can cause a suitably designed tether to lose a domain having affinity for a target. Alternatively, the cleavage can create a free terminus for an epitope that requires such a terminus for binding thereby conferring a binding specificity not present in the unmodified tether. Additional binding specificity can also be conferred by modifications in which the reporter molecule binds to the tether or enzymatically modifies the tether in such a manner that another entity is added (e.g., birA catalyzes addition of biotin). In all of these situations, complexes bearing modified tethers can be separated from complexes bearing unmodified tethers by affinity purification to the target for which binding affinity is lost or acquired. If binding affinity is acquired, complexes binding to the target are retained and other complexes discarded. Conversely if binding affinity has been lost, complexes binding to the target are discarded and other complexes are retained. Affinity purification can be performed by similar approaches to those employed in ESL or phage-display methods except that the moiety binding to the affinity reagent is the tether rather than compounds being screened. Methods from the field of protein purification can also be employed (e.g., immobilization of the target to a column).

Alternatively, a novel and particularly effective separating method uses a target labelled with a dense metal, such as gold. The method exploits a change in buoyant density imparted upon receptor/dense metal binding. Complexes to be screened for binding to the receptor are first blocked for nonspecific binding, e.g., with BSA. The blocked complexes are contacted with receptor labelled with a dense metal. Labelling can be accomplished, for example, by binding of an anti-Ig antibody labelled with colloidal gold to an antibody receptor. Binding supports are separated from nonbinding supports by centrifugation through density-adjusted media. For example, phosphate-buffered sucrose (about 40 Brix units) is suitable. Bound supports migrate to the bottom of the tube whereas nonbinding supports remain on the surface or migrate to an intermediate point of the tube.

Figure 3A:
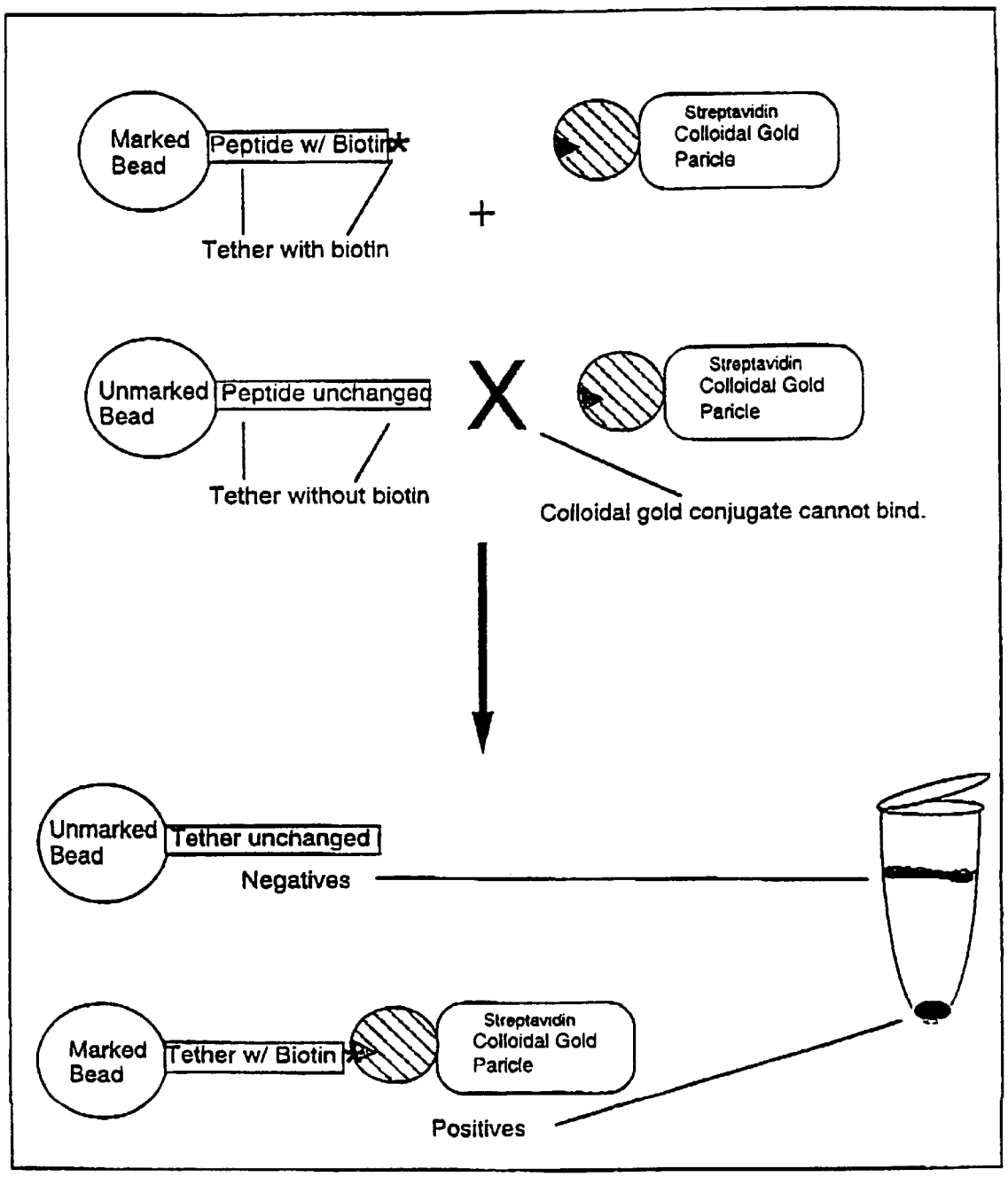
FIG. 3A and FIG. 3B: Schemes for separation of marked and unmarked supports using dense metal labelled receptor.
Figure 3B:
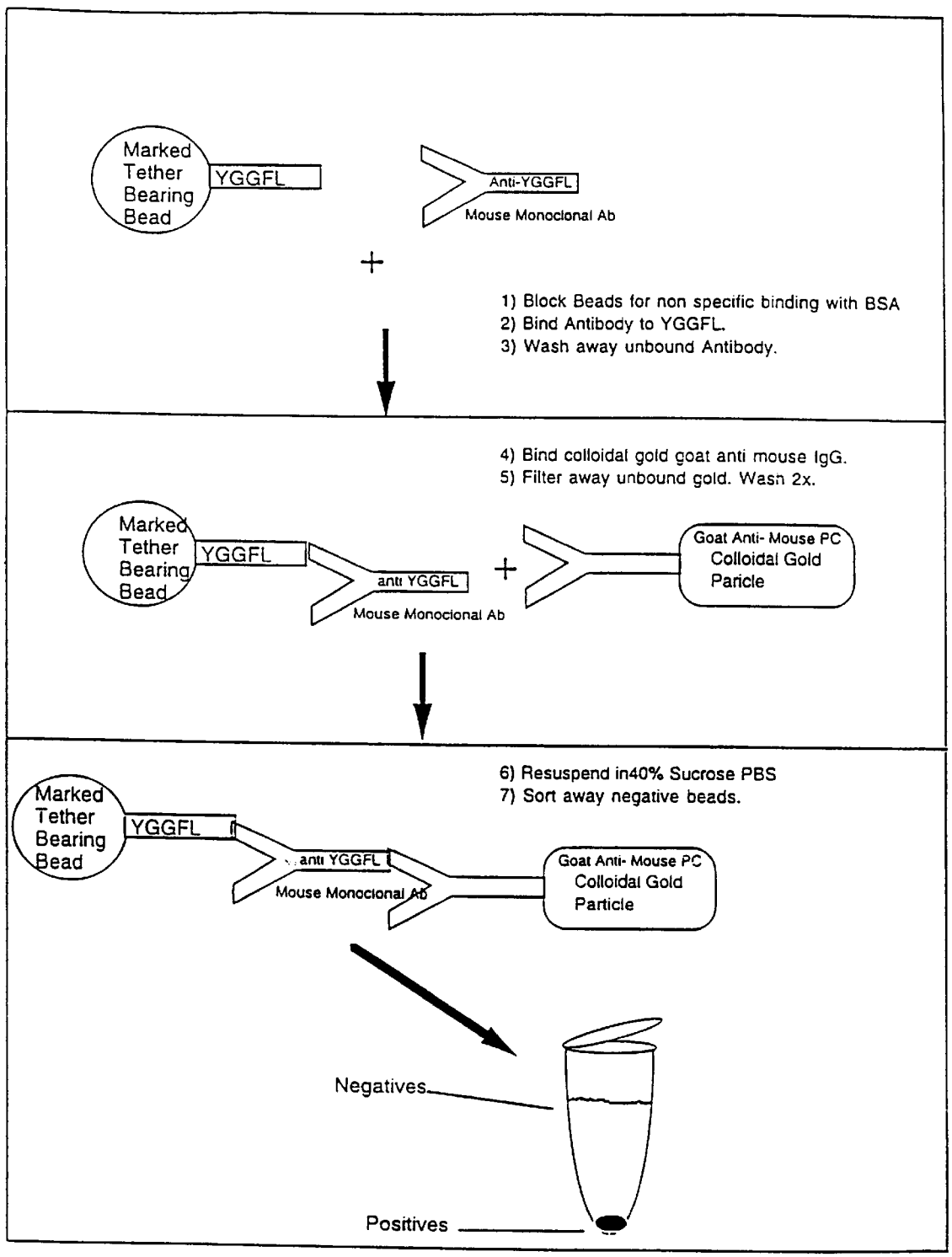

This separation method is illustrated in FIGS. 3A and B. The upper part of FIG. 3A shows beads with a peptide tether. One tether is marked with biotin and the other is not. The support with the marked tether can bind through the biotin to a streptavidin colloidal gold particle. In the lower part of the figure, supports bearing modified tethers are separated from supports bearing unmodified tethers by centrifugation. FIG. 3B shows an alternate scheme in which a support bears a tether modified to acquire affinity for the anti-DynB antibody. Initially the support is incubated with BSA to block nonspecific binding. The support is then contacted with the antibody to which it binds via the tether. After washing away unbound antibody and support, the antibody is labelled with gold by binding of a goat anti-mouse colloidal-gold labelled antibody. The complexes are resuspended in approximately 38% sucrose phosphate-buffered saline and centrifuged at 15,000 g for 1 min. Supports binding to the target antibody are then recovered from the bottom of the tube.

Where the modification of the tether confers a change in spectral properties of the tether different approaches are used for separating complexes bearing modified and unmodified tethers. For example, complexes can be separated into different fractions by FACS™. Alternatively, the complexes can be plated in a soft agar layer and modified supports picked by color. For example, this approach works well when the reporter molecule binds the tether and also has an enzymatic activity conferring an easily detectable color change on a substrate (e.g., alkaline phosphatase).

The screening methods described above usually isolate a collection of different library members. Individual members are then isolated from the collection by means such as infinite dilution, micromanipulation, or fluorescence activated cell sorting (FACS) (*Methods Cell Biol.* 33, (Darzynkiewicz & Crissman eds., Academic Press); Dangl & Herzenberg, *J. Immunol. Methods* 52, 1–14 (1982).

E. Tag Decoding and Compound Synthesis

When complexes bearing modified tags have been isolated, the tags are decoded by conventional means. For example, if the tags are nucleic acids, they can be decoded by PCR amplification and sequencing. Other types of tags can be decoded by, for example, mass spectrometry, FACS™, gas chromatography or HPLC. The information from decoding the tag identifies the compound (or component(s) thereof) originally from the same complex as the tag. Based on this information the compound can be synthesized de novo. For example, if the compound is a peptide, it can be synthesized on a peptide synthesizer. If the compound is a benzodiazeapine, it can be synthesized by conventional organic chemistry. If a substantial collection of compounds are identified, the compounds can be resynthesized on supports and rescreened by reiteration of the same approach.

F. Variations

1. Secondary Reporters and Signal Amplification

The primary reporter molecule produced in response to signal transduction can modify the tether of a complex either directly or indirectly. By indirect modification, it is meant that the primary reporter molecule modifies a second reporter molecule, which in turn modifies the tether. For example, as an alternative to direct modification by tPA of a tether comprising a tPA substrate, the tPA can be used to convert plasminogen to plasmin, and the latter can modify a tether comprising a plasmin substrate (Wrighton, in *Methods in Molecular Biology*, Vol. 7, Ch. 16 (Humana Press, Inc. Clifton, N.J., 1991)). Such is achieved by including plasminogen in the medium in which cells and complexes are mixed. When tPA is released by a responding cell, the plasminogen in the vicinity of the cell is converted to the active protease, plasmin, which then acts on the local tether(s). This cascade provides a more active marking of the complexes bearing transducing compounds thereby increasing the sensitivity (i.e., absolute number of true positives recovered). However, in some instances, the possibility of cross-talk may also be increased. In a variation, one reporter molecule, whose expression is coupled to activation of a receptor, can be a regulatory molecule that induces synthesis of another reporter molecule, which has the capacity to modify tethers.

Of course, these principles can be extended to a cascade of reporter molecules. For example, expression of a first reporter molecule can be coupled to transduction through a cellular receptor, the first reporter molecule can induced synthesis or modify a second reporter molecule and the second reporter molecule can induce or modify a third reporter molecule, which modifies a tether.

Reporter Systems Employing Site-Specific Recombinases

In a variation of the above approach, reporter cells contain two constructs, which can be present on the same or different replicons. One construct encodes a site-specific recombinase operably linked to regulatory sequences that result in expression of the recombinase when a target receptor on the reporter cells is activated by a transducing compound. Examples of site-specific recombinases include Cre and Flp (see Kilby et al., *Trends in Genetics* 9, 413–421 (1993)).

The regulatory sequences depend on the target receptor. For example, to screen for activators of 7TM receptors, the recombinase is placed under the transcriptional control of a promoter which responds to 7TM receptor signalling. Examples include the fos promoter, or an engineered promoter composed of repeating cyclic AMP response elements, or the Fus1 promoter if the 7TM receptor is expressed in yeast reporter cells. As a further example, to screen for activation of a T-cell receptor, the recombinase can be linked to an NFAT promoter. In a further variation, the site-specific recombinase can be expressed as a fusion protein with a target receptor, such that the recombinase is inactive in the fusion protein unless the fusion protein is bound to a ligand, which causes steric changes that activate the recombinase. Activation of recombinases fused to ligand binding domains of nuclear receptors on ligand binding has been reported. See Logie & Stewart, *Proc. Natl. Acad. Sci. USA* 92, 5940–5944 (1995); Metzger et al., *Proc. Natl. Acad. Sci. USA* 92, 6991–6995 (1995). Suitable nuclear receptors include estrogen, glucocorticoid and androgen receptors.

The other construct in the reporter cells contains a gene comprising a coding sequence for a reporter molecule, a promoter (usually strong and constitutive, such as an SRα or CMV promoter) and an inactivating sequence present in either the coding or noncoding sequence of the gene, which prevents expression of the coding sequence from the promoter. The inactivating sequence can be virtually any sequence which disrupts expression of the coding sequence (e.g., by insertion of a stop codon) or inhibits transcription of the downstream reporter gene. Preferably, the inactivating sequence is itself capable expressing a selectable marker. Selection for this marker ensures retention of the inactivating sequence in the second construct until use in the assay thereby reducing background levels of reporter molecule.

The inactivating sequence is flanked by specific sites recognized by the site-specific recombinase, which allow excision of the inactivating sequence when the site-specific recombinase is expressed. Suitable site-specific recombinases are Cre and Flp, which recognize loxP and frt sites respectively. Selection of an inactivating sequence may also select for variants of loxP and frt that are less susceptible to recombinase action, thereby reducing background levels of the second reporter. See Senekoff et al., *J. Mol. Biol.* 201, 405–421 (1988). Cre and Flp recombinases can also be mutagenized to give less active variant forms, if desired.

Excision of the inactivating sequence results in expression of the reporter molecule which can be released from cells and modify the tether of the complex bearing the transducing compound. Signal transduction in just a few or even single cells causes a permanent phenotypic switch of gene expression, and results in the conversion of a short-term signal into a long-term response which can be amplified. Also, because the reporter can be expressed from a strong constitutive promoter rather than a weak regulatable promoter (e.g., fos or jun), the reporter can be expressed in larger amounts that a reporter directly coupled to signal transduction.

In a further variation, a construct encoding a deactivated reporter gene as described above also contains regulatory sequences that render expression of the deactivated gene inducible on signal transduction through a cellular receptor. The cells also contain a second construct encoding a recombinase enzyme, expressed from an inducible promoter, such as a tetracycline-sensitive promoter (Gossen et al., *Proc. Natl. Acad. Sci. USA* 89, 5547 (1992)). In the presence of inducer, the recombinase is expressed and excises the inactivating sequence from the reporter gene, allowing the reporter gene to be expressed to generate functional reporter molecules when the cellular receptor is activated by a transducing compound. In general, the inducer is added to cells shortly before releasing compounds from the complexes, thereby arming the reporter molecule immediately before the assay for transducing activity is performed. Accordingly, the background level of functional reporter molecule in the absence of transducing compound is reduced.

To show that Cre functions in CHO reporter cells, a cell line was stably transfected with a construct containing from 5' to 3', a CMV promoter, a puromycin-resistance encoding sequence flanked by loxP sites and a luciferase coding sequence. Transient transfection of this cell line with a plasmid expressing Cre from the strong CMV promoter resulted in a 50-fold increase in luciferase expression. A similar experiment was performed with a CHO cell line transfected with a β-galactosidase reporter plasmid in which the β-galactosidase coding sequence was interrupted by a neomycin gene cassette flanked by frt sites, recognition sites for the Flp recombinase. Transient transfection of this cell line with a plasmid expressing Flp resulted in a 1000-fold increase in beta-galactosidase activity). To show that Cre recombinase functions in yeast, Cre was placed under the yeast GAL1 promoter and transformed into a strain containing a URA3 gene flanked by loxP sites. Cells were grown in raffinose-containing medium, and the Gal1 promoter was induced by adding galactose. After 15 minutes of induction, over 60% of the yeast cells had undergone recombination and lost the URA3 marker. By 30 min, over 90% of the cells in the culture had recombined.

2. Partial Cleavage of Compounds From Complexes

The release of only a portion of a compound from a complex is often desirable. Controlled, partial release of the library compound allows rescreening of the positive beads to confirm that they are truly positive or to enrich for the best transducing compounds. Rescreening may be desirable in instances where the primary screen is done at high bead density, and cross-talk may occur. In these instances, the positive complexes are selected and rescreened at a lower density, thus reducing the likelihood of cross-talk and false positives. Partial cleavage can be achieved by controlling of reaction conditions (e.g., temperature, time, frequency of radiation, amount of enzyme added). Alternatively, compounds can be attached to two or more different linkers on the same complex, which linkers are susceptible to cleavage by different mechanisms, thereby allowing separate release of first and second aliquots of compound. For example, this can be accomplished by having two linkers both of which have photocleavable groups, but in one of which the photocleavable group is initially masked. After release of first aliquots of compounds by cleavage of the unmasked linker, the masked linker is unmasked and second aliquots of compounds can be released.

3. Regeneration of Tethers

If the same complexes are to subjected to more than one round of screening, it is preferable to regenerate the tethers between rounds. If tethers are regenerated, a compound must independently survive both screening rounds to be scored as a transducing compound. As an example, regeneration can be achieved by covalently attaching biotin molecules to the complexes, followed by addition of streptavidin, and then a fusion protein comprising a C-terminally biotinylated tPA substrate peptide linked to an epitope for a known target.

This creates a sandwich of bead-biotin-streptavidin-biotinylated tPA substrate/epitope. Primary screening is performed as described above, and after selection, the marked complexes (tPA tether cleaved) are regenerated to the unmarked state by heating or extracting the complexes to remove the streptavidin and residual tPA substrate peptide. These complexes can then be re-exposed to biotin to which fresh streptavidin and biotinylated tPA substrate/epitope can be attached.

In a variation, complexes bear at least two different tethers susceptible to modification by two different reporter molecules. Complexes are exposed to first and second reporter cells, each having the same receptor, but differing between the reporter molecules coupled to activation of the receptor. Activation of the receptor in a first round of screening results in export of a first reporter molecule, which modifies a first tether on the complexes. Activation of the receptor in the second round of screening results in export of a second reporter molecule, which modifies the second tether on the complexes.

4. Controlled Release of Reporter Molecule

As noted above, the sensitivity of the assay can sometimes be increased by allowing the reporter molecule to accumulate in cells before the controlled lysis of cells and concomitant release of a burst of reporter molecules. One method of achieving controlled release of a reporter molecule is to link the reporter molecule to a phospholipid anchoring domain and signal secretion sequence as described in commonly owned copending U.S. Ser. No. 08/309,345, filed Sep. 19, 1994 (incorporated by reference in its entirety for all purposes). Usually, the anchoring domain is linked to the C-terminus of the reporter molecule and the signal sequence to the N-terminus of the reporter. The signal sequence directs secretion of the reporter molecule from the cell where it becomes attached to the surface phospholipid layer by the anchoring domain. Controlled release can then be achieved by cleaving the bond between phospholipid and the reporter molecule by addition of a phospholipase to the matrix in which cells and complexes are contacted. For example, the anchoring sequence from the human placental alkaline phosphatase gene CLEPYTACDLAP-PAGTTDAAHPGRSVVPALLPLLAGTLLLLETATAP (SEQ ID NO:2) or a subsequence thereof, capable of anchoring the receptor is suitable. Anchored reporter molecules can released from cells by addition of the enzyme phosphoinositol phospholipase C.

In a variation, reporter cells encode first and second reporter molecules. The coding sequence for the first reporter molecule is operably linked to regulatory sequences that place expression subject to activation of the receptor. The first reporter molecule encodes a protein that can effect lysis of the cell, such as phage λ lytic protein. The second reporter molecule is constitutively expressed and has a property that renders it capable of modifying tethers. On activation of the receptor, the first reporter molecule is expressed, causing lysis of the cell and release of the second reporter molecules, which modifies the tether of beads in proximity of the cell.

5. Coincidence Circuits

The specificity (ratio of true positives to false positives) of the above methods can be increased by requiring that a compound transduce two events for the tether on the complex bearing the compound to be modified. For example, the two events can be the generation of a primary and secondary reporter molecules, whereby the primary reporter molecule modifies the secondary reporter molecule to a form in which the latter can modify the tether. Alternatively, the secondary reporter molecule might function to release the primary reporter molecule from phospholipid anchorage. The primary and secondary reporter molecules should be expressed from constructs susceptible to induction by the same receptor. However, the primary and secondary reporter may be in the same or different cells, bearing the receptor. If the two reporters are expressed in separate cell types, the two cell types are mixed before releasing compounds from complexes. The two reporters are both expressed from regulatory sequences activated by the receptor, but the regulatory sequences need not be the same for the two reporters, and are preferably different. For example, if the receptor is a G-protein linked receptor, the first and second reporter molecules can be expressed from fos and jun regulatory sequences respectively. The use of different regulatory sequences for expression of the two reporter molecules can reduce background signal not due to receptor transduction.

A different type of coincidence circuit can be used to select for compounds specific for a particular receptor. This circuit specifically selects for compounds that transduce a signal through a first receptor but which are unable to transduce a signal through a second receptor. This circuit is designed by linking the first and second receptors to expression of first and second reporter molecules, of which the second inactivates the first rendering the latter incapable of modifying the tether. For example, if the first reporter molecule is a proteinase, tPA, the second reporter molecule can be a proteinase inhibitor, such as aprotinin. In this type of coincidence circuit, the first and second receptors are different from each other and the first and second reporter molecules are expressed from constructs bearing regulatory signals appropriate for signal induction by the respective receptors. The second receptor can be a variant form of the first receptor (e.g., one or a few amino acid changes), a distinct, but related receptor (e.g., two G-protein linked receptors) or entirely unrelated, depending on the degree of specificity for which selection is desired. The first and second receptors (and respective reporter constructs) can be expressed from the same or different cell types. If expressed from different cell types, the first and second reporter molecules should be secreted, or otherwise released from the respective cells, for inactivation to occur.

6. Screening in Wells of Assay Plate

In a further variation, complexes are contacted with cells in the wells of an assay plate, and compounds are then released from the complexes. In this approach, complexes can be contacted with cells in a liquid allowing free diffusion of the compound. The wells confine a reporter molecule released from a cell such that it can only modify the tethers of complexes present in the same well. If there is only one complex per well, only that complex can be modified by the receptor. After an appropriate period of incubation, complexes are removed from the wells and complexes having modified tethers are isolated by virtue of the modified tethers.

Usually an initial round of screening is performed in which there are multiple complexes present in most wells in the array (e.g., about 10 to 1000 per well). In this situation, if a well contains a single complex bearing a transducing compound, any complex in the well can be modified. However, in wells lacking a complex bearing a transducing compound, no complexes are modified. After incubation and pooling of complexes, the complexes bearing modified tethers are enriched for transducing compounds.

The enriched pool of transducing compounds can be subjected to a second round of screening. This is most readily performed when the compounds are attached to support in such a manner that the compounds can be released in two aliquots. In this situation, the second screening commences by regenerating the modified tether. The enriched complexes are then contacted with fresh cells in the wells of a fresh assay plate, and the second aliquot of compounds is released from the cells. In the second round of screening, there are fewer complexes per well (preferably, most wells have only one complex), so that a greater degree of enrichment is obtained.

A suitable assay plate resembles a conventional microtiter dish except that the wells are smaller and more numerous. For example, an assay plate containing $10^6$ wells in an array of 1000 by 1000, each well having dimension of 100 $\mu$m×100 $\mu$m×100 $\mu$m (1 nl) measures 10 cm by 10 cm and can be fabricated by photolithographic techniques. The wells needed not be arranged in any particular geometric configuration. The library of compounds can be synthesized on monobeads and about $10^8$ beads can be conveniently screened on a single plate at an average density of about 100 beads per well. Each 10 $\mu$m mono bead has ~10 fmol of synthesis sites. Given a synthetic yield of 50%, and a two stage release in equal aliquots, each aliquot of compound released is 2.5 fmol per bead. This quantity, when released into an assay volume of 1 nl produces a concentration of 2.5 $\mu$M.

The beads can be loaded into the wells in bulk by settling from a concentrated slurry. Each well contains from about 1–1000 reporter cells, and preferably about 100 cells. Thus, for example, about $10^8$ monobeads and $10^8$ cells in a volume of about 1 ml are loaded on to an assay plate. The first aliquot of compound is released from the beads (e.g., by exposure of a photocleavable linker to light), and the assay is allowed to run a sufficient time for expression of the reporter molecule to be established.

Assuming 1 active bead per million, screening $10^8$ beads activates the reporter in about 100 wells. Each active well contains 100 beads, only one of which carried an active compound, but all of which become marked by the reporter cells. This round of screening produces a total of ~10,000 marked beads (100 true positives). All $10^8$ beads are then removed en masse from the assay plate and beads having modified tethers are isolated. The $10^4$ recovered beads are then stripped of the modified tether and a fresh tether is regenerated on the beads. These beads (along with a mass of carrier beads to aid in handling the small numbers of tiny beads) are reloaded into the assay plate along with a fresh batch of reporter cells. Because $10^4$ beads are loaded into a plate with $10^6$ wells, the probability is low that any well receives more than one bead. The second aliquot of compound is released (e.g., by exposure of a second photocleavable linker to a different wavelength) and the assay repeated. Once again, the beads are washed from the plate, and beads bearing modified tethers are isolated. The synthesis history of the beads bearing transducing compounds can then be decoded from the tags.

II. Other Screening Methods

The methods described so far have screened library members comprising a compound, a tag and a tether, linked to a support and/or each other. One of the basic principles of this method, i.e., using a reporter molecule to modify a tether can also be exploited to screen other types of library.

(a) Supports Bearing Compounds and Tethers but Lacking Tags

In one method, libraries are produced having members comprising a support bearing a compound to be screened (differing between different members) and a tether (the same for different members) but lacking a tag identifying the compound. Such libraries can be synthesized using a similar divide-and-pool approach as is employed for ESL libraries above, with the exception that all steps associated with synthesis of tags are omitted. Synthesis of nontagged libraries is also described by Lam, WO 92/00091 and Houghten, U.S. Pat. No. 4,631,211 and WO 92/09300. As will become apparent, it is important that the supports in such libraries bear sufficient compound both for activation of a receptor and for direct analysis of the compound to determine its identity.

Such libraries are screened by a generally similar approach to that employed for coded libraries. Specifically, the libraries are contacted with reporter cells in any of the formats discussed above. Compounds are then partially cleaved from the supports (i.e., the cleavage reaction does not proceed to completion). Cleaved compound diffuses to a receptor on reporter cells, where, if the compound has capacity to transduce a signal, the compound induces expression of a reporter molecule. The reporter molecule then modifies, directly or indirectly, the tether of the support of the compound transducing the signal.

Supports bearing modified tethers are separated using the same methods as described above. The identity of compounds is determined by direct analysis of residual compound borne by the supports. Such analysis can take the form of, for example, peptide sequencing, infra red analysis or mass spectrometry, depending on the nature of the compound.

(b) Libraries of Cells Producing Compounds

In another method, the libraries have members comprising cells producing compounds to be screened. The compounds may be cell surface peptides encoded by the genome or a plasmid within the cell. However, more frequently, the compounds are secondary metabolites, such as polyketides, which are produced by the cells' enzymatic apparatus but which are not directly encoded by the nucleic acids within the cell. Preferably, the compounds are secreted from the cells producing them.

In some methods, cells producing the compounds to be tested are selected, or otherwise genetically modified, so that they express a cell surface tether. Such cells are then contacted with reporter cells in any of the formats described above. Active compounds from the library transduce expression of reporter molecules, which modify the tethers of cells producing the respective compounds in similar fashion to that described above. Further, cells bearing active compounds can be isolated by virtue of their modified tethers. The difference from the above methods arises in how compounds are identified once cells have been identified. For cells producing compounds representing secondary metabolites, the identity of a compound is determined by propagating a homogeneous culture of a cell having a modified tether, purifying the compound from the culture, and directly analyzing the compound (e.g., by peptide analysis, mass spectrometry or infrared spectroscopy).

Figure 4:
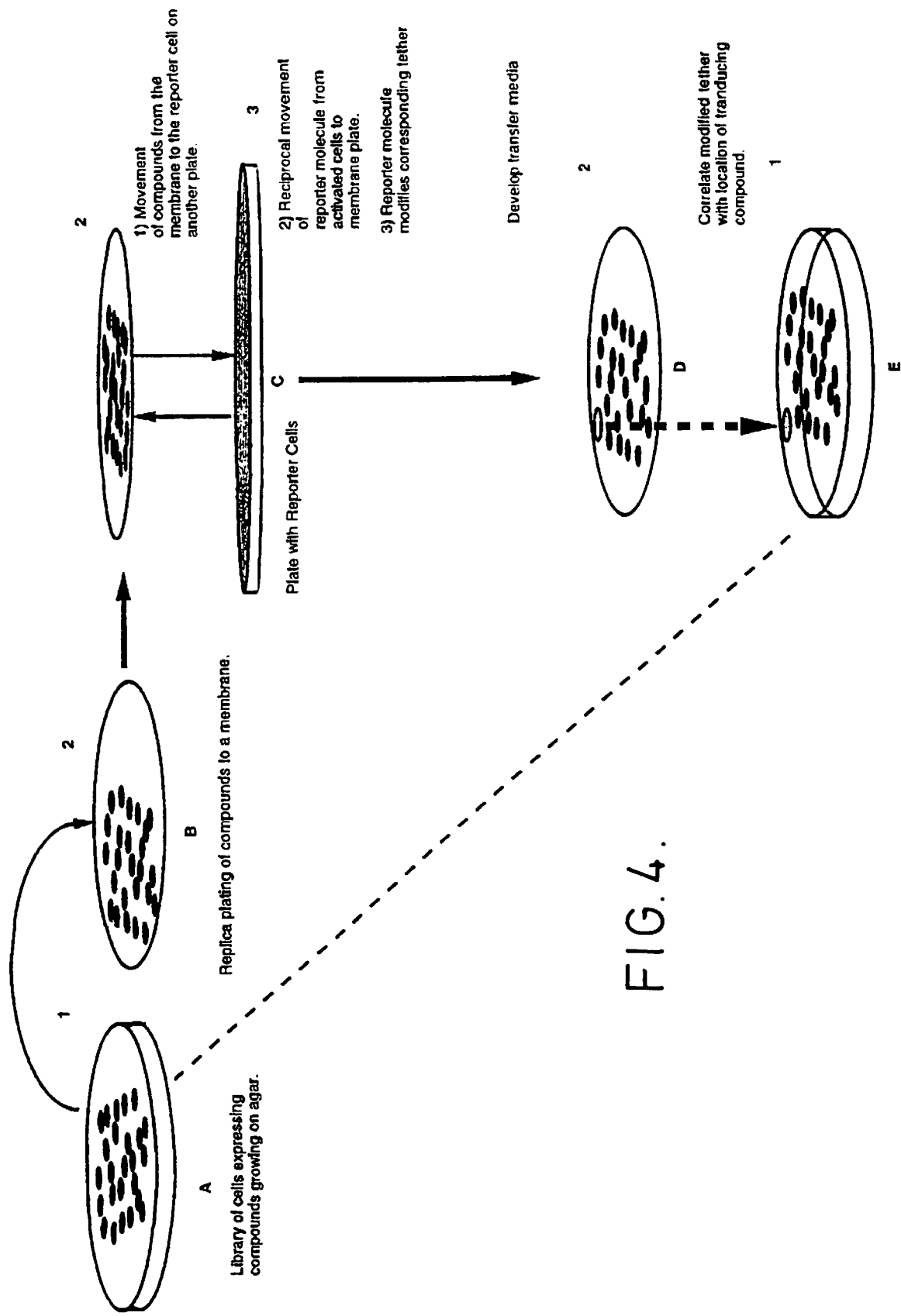
FIG. 4: Scheme for screening a library of cells producing compounds for transducing activity.

In other methods (see FIG. 4), cells producing compounds to be tested need not have tethers directly affixed to the cells. In such methods, the cells producing the compounds to be screened are plated as an array of discrete colonies (e.g., on agar plates). The colonies are then replica plated onto a membrane, such as a nitrocellulose filter that has been pre-coated with a tether molecule that subsequently blocked against non-specific binding with BSA. If the compounds to be screened are not secreted by the cells producing them, the cells should be artificially lysed after transfer to the membrane. Transfer produces an array of compounds immobilized to the membrane in which the respective positions of the compounds in the array correspond to the respective positions of colonies on the original cell culture plates.

The membrane bearing the array of compounds is contacted with a culture of reporter cells having the characteristics described above. The compounds then diffuse from the filter matrix towards the reporter cells. The activating compounds then cause the reporter cells to respond by producing reporter molecules which, in turn, diffuse back towards the location from which the activating compounds originated. Active compounds in the array transduce a signal in the reporter cells causing release of a reporter molecules, which modifies the membrane at a site at, or proximate to, that at which the compound transducing the signal is attached. For example, if the reporter molecule is BirA and the membrane is impregnated with a substrate for BirA, the modification constitutes attachment of a biotin molecule to the membrane. The marked membrane is separate from the reporter cells and if, necessary, developed (e.g., by exposure to labelled avidin) to reveal the location of the markings. The membrane is aligned with the original plates of colonies producing the compounds and colonies aligning with marked regions of the membrane are picked. If markings are close together and precise identification of aligned colonies is difficult, picked colonies are rescreened by the same approach. Finally, a colony corresponding to a marked region is propagated to produce sufficient amounts of compound for direct analysis of the compound to reveal its identity.

(c) Use of a Membrane as a Tether

Many of the principles discussed above, can be exploited in a further variation, in which complexes bearing compounds and tags are screened in an array format immobilized to a membrane. In this situation, the area of the membrane proximate to each complex effectively forms a tether for that complex. The membrane format is also effective for screening complexes having a compound, a tag and a separate tether.

In either situation, the array of compounds is provided on a membrane, such as the nylon or nitrocellulose membranes used in conventional blotting experiments. Discrete aliquots of each compound usually occupy discrete sites in the array, although some overlap of sites is permissible if several rounds of screening are to be performed. It is not necessary to know in advance which compound occupies which site in the array, or for the sites to form any particular geometric configuration.

Often the compounds are synthesized as ESL libraries (i.e., an aliquot of each compound is attached to a bead bearing a tag identifying the synthetic route of the compound). The ESL libraries may or may not have tethers of the kind described above. About $10^8$ monobeads can be immobilized on a membrane surface of 320 cm$^2$ (16×20 cm) with beads separated on average about 10 microns from their nearest neighbor. Beads can be deposited on the membrane suspended in sucrose buffer as a slurry under vacuum. Visible microscopy is used to check the distribution of beads on the membrane. If the distribution is uneven, more buffer is added to the membrane, and the beads are resuspended until a monolayer is achieved. Binding of the beads to the membrane can be strengthened by irradiation or chemical conjugation.

The membrane bearing an array of compounds is laid down on a surface of reporter cells of the kind described above, and compounds are released from the membrane. Sometimes first and second aliquots of compounds are attached by different linkers and only the first aliquot is released in the first round of screening. Released compounds diffuse into contact with cells, and active compound(s) transduce a signal through a cellular receptor resulting in release of a reporter molecule from reporter cells. The reporter molecule diffuses toward the membrane and modifies either the tether of the complex from which the active compound was released or a site on the membrane proximate to the location of the active compound. This depends on the selection of reporter molecule, and whether the complexes being screened have tethers. SEAP is a suitable reporter molecule to mark a membrane. SEAP is very stable once bound to a nylon membrane surface (Kirchhoff et al., *TIGS*, (June 1995)). The membrane is peeled off the agar overlay and developed for SEAP activity in NBT/BCIP buffer (pH 9.8) to visualize the region of the membrane containing active beads.

If the modification is designed to occur to the membrane, modified areas of the membrane are cut out and supports recovered. The supports can then, if desired be subjected to a further round of screening, which proceeds as the first round, except that the second aliquots of compound are released. If the modification is designed to occur on support-bound tethers, supports bearing modified tethers are isolated as previously described. If the supports still bear a second aliquot of the compounds, the supports can be subjected to a second round of screening before decoding of tags to reveal the synthesis route of active compounds.

(d) Screening for Compounds Having Receptor Binding Activity

The strategy for identifying compounds that transduce a response through a receptor can be adapted to identify compounds that merely bind to a receptor irrespective of transducing activity. Libraries of compounds can be provided in the same format described above, (e.g., complexes comprising a support bearing a compound, a tag and a tether). The libraries are screened by contacting these primary complexes with secondary complexes. The secondary complexes comprise a support, such as a bead, a receptor (or a ligand-binding domain thereof), a ligand to the receptor and a reporter molecule. Either the ligand or the receptor (but not both) is irreversibly immobilized to the support. The immobilized moiety is then specifically but reversibly bound to whichever moiety is not immobilized. That is, if the receptor is immobilized, it is reversibly bound to the ligand and vice versa. optionally, multiple ligands can be bound to the same receptor or vice versa, thereby increasing the avidity of binding. Bivalent or higher multivalency is an advantage for ligand-receptor pairs having low affinity interaction since it reduces dissociation of pairs in the absence of competing compounds but does not prevent dissociation in the presence of a competing compound. Whichever moiety is not immobilized to the support is linked to the reporter molecule in such a manner that the combined molecule retains the functions of both of its constituents. For example, if the receptor is immobilized, the ligand is linked to the reporter, such that the ligand retains its ability specifically to bind to the receptor and the reporter retains its ability to report. The two components can be linked as a fusion protein or by chemical crosslinking, antibody capture on common fused epitopes, or attachment of several copies of each molecule to nano-supports, such as colloidal particles.

The format in which the receptor is irreversibly immobilized to the support is particularly useful when a soluble form of the receptor is not easily available, as is the case for seven transmembrane receptors and ion channels. In this situation, the support in the secondary complex can be a cell expressing the receptor on its surface.

After contacting the primary complexes with secondary complexes, compounds can be released from the primary complexes and diffuse into contact with the secondary complexes. A compound having affinity for the receptor, competitively displaces either the ligand or receptor (whichever is not immobilized) from the secondary complexes. The displaced ligand or receptor is linked to a reporter molecule, which after release from its secondary complex, is free to diffuse into contact with the primary complex from which the active compound was released and modify the tether of the same. (Intact secondary complexes are too massive to diffuse into contact with the tethers of primary complexes at significant frequency.) Other aspects of the screening method, such as suitable matrixes or wells for contacting primary and secondary complexes, and methods of identifying complexes having modified tethers are as described in other methods of the invention. More flexibility is possible in choice of reporter molecules because in the present methods it is not necessary that these molecules be proteins.

Figure 5A:
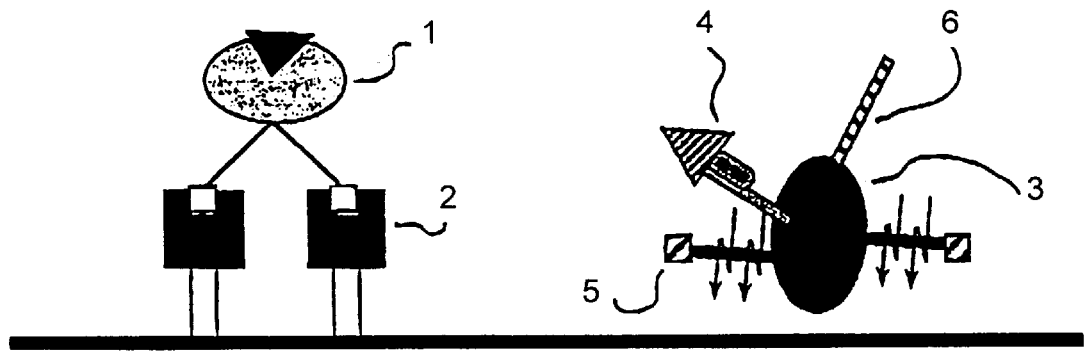
FIG. 5A through FIG. 5C: Scheme for screening a library for compounds that bind to a receptor by a competitive binding assay.
Figure 5B:
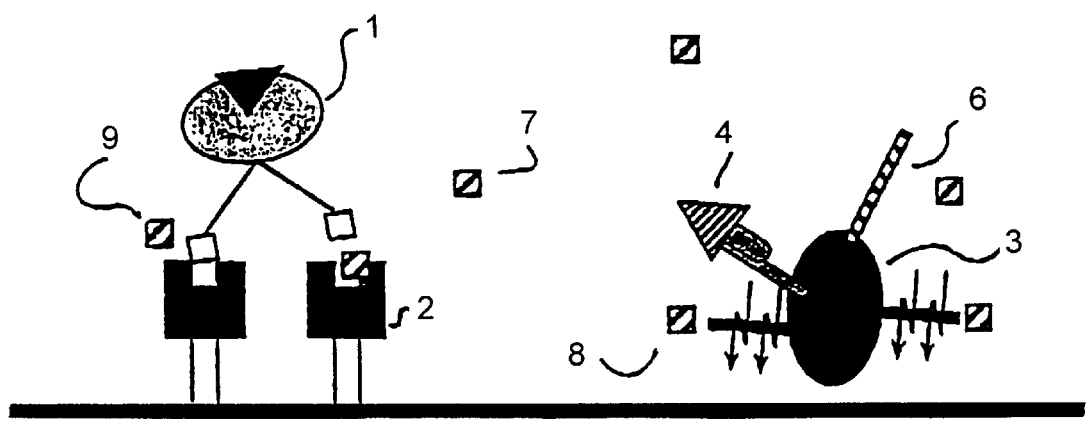
Figure 5C:
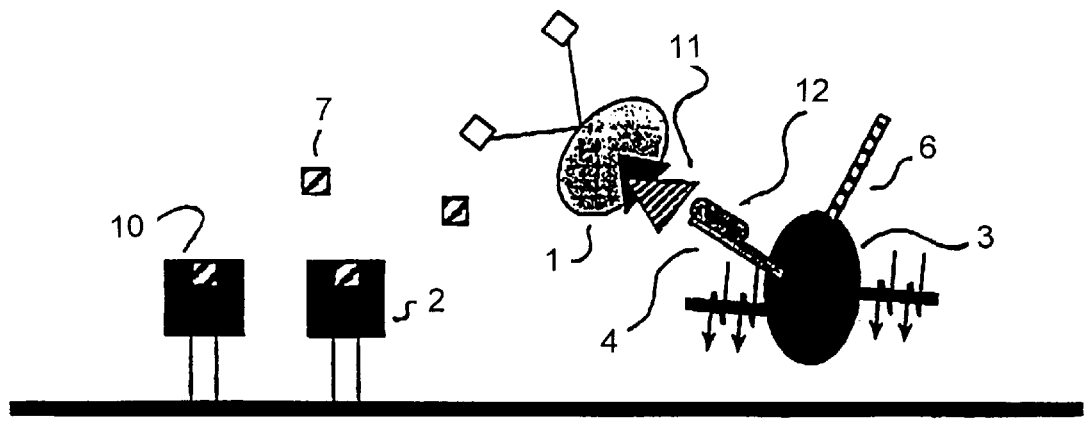

FIG. 5A through FIG. 5C show an exemplary competitive binding assay. FIG. 5A represents the situation before compounds are released from supports. The reporter-fusion (1) is bound to its corresponding immobilized receptor pair (2). Nearby is a bead (3) comprising a tether (4), a compound on a cleavable linker (5) and a tag (6) correlating to compound (5). FIG. 5B represents the events after the compounds are released (8). A compound having affinity for the receptor (7) diffuses from its support (3) and displaces the reporter-fusion (1) from the receptor pair (2). FIG. 5C represents the soluble reporter fusion (1) acting on (11) the tether (6) leaving a modified tether (12).

As in other methods, the reporter molecule can modify the tethers of supports bearing active compounds indirectly through activation of a secondary reporter molecule. For example, a first reporter might be specific protease fused to the target receptor bound to an immobilized ligand. Competition-mediated release of the protease fusion then allows the proteolytic release of a large amount of reporter two which is fused via a peptide containing the protease recognition site to a support. Reporter two then marks the supports of the primary complex. Thus, a stoichiometric release of reporter one results in a catalytically-amplified release of reporter two, thereby amplifying the response signal.

In another amplification format, the reporter molecule can be a ligand or other agonist (e.g., a synthetic short peptide) of a secondary receptor present on reporter cells of the kind described above. Release of a compound from a primary complex displaces a first reporter molecule from a secondary complex. The reporter molecule then diffuses into contact with a secondary receptor on a cell, and transduces a signal through the secondary receptor causing release of a second reporter molecule from the cell. The second reporter molecule then modifies the tether of a primary complex bearing the compound that displaced the first reporter molecule.

III. Screening for Inhibitors of Enzymes

Some of the principles underlying the methods of screening compounds for signal transducing capacity can also be exploited to screen compounds for capacity to inhibit a selected enzyme. In some such methods, the compounds to be screened are again provided as components of complexes that also bear tags serving to identify the compounds and a tether susceptible to modification. The tether is chosen to be susceptible to modification by the enzymatic activity to which it is desired to isolate inhibitors. Again, the tether is usually the same for all complexes in the library. Such libraries of complexes are produced by the same procedures as described above.

Compounds are screened for enzymatic activity by contacting the complexes bearing the compounds with enzyme in a matrix, such as agar or agarose. Before, concurrent with, or after contacting complexes with enzyme, the compounds are released from the complexes (e.g., by cleavage of a photocleavable linker). Release should occur after compounds have been incorporated into the matrix. Release can be partial or complete. If the enzyme is contacted with complexes before release of compound, it is desirable that the enzyme activity initially be substantially absent. This can be achieved by performing the contacting at low temperature, and/or in the absence of a cofactor. After release of compounds, the enzyme can be activated by raising the temperature or impregnating the matrix with the cofactor.

The matrix allows diffusion of the compound over short distances commensurate with the dimensions of the complex, but substantially prevents diffusion of the compound to neighboring complexes. After release, a compound diffuses forming a halo around the complex from which it was released. If the compound has enzyme inhibiting activity, the halo of compound protects the tether of the complex releasing the compound from modification by the enzyme. For compounds lacking such activity, the tethers of complexes releasing the compounds are modified by the enzyme. Thus, the result of contacting complexes with the enzyme is that a subpopulation of complexes have modified tethers and a second subpopulation have unmodified tethers and the second subpopulation is enriched for complexes that originally bore compounds with inhibiting activity. The probability of a tether undergoing modification is substantially higher (e.g., about 5-, 10, 50 or 100% higher) for complexes having compounds lacking inhibiting activity than for complexes having compounds with inhibiting activity. Complexes having unmodified tethers can be subjected to further rounds of screening using the same principles. Ultimately, individual complexes bearing unmodified tethers are isolated and the identity of compounds determined from the tags.

Selection of the tether is, of course, dependent on the nature of the enzyme for which isolation of inhibitors is desired. If the enzyme is a protease, the tether should be a protein including a site recognized by the enzyme. If the enzyme is a DNA polymerase, the tether should be a nucleic acid fragment capable of being extended by the polymerase. If the enzyme is a kinase, the tether should be a peptide having a site susceptible to phosphorylation. If the enzyme is a phosphatase, the substrate should be a peptide bearing a phosphate group.

Many of the variations and alternative described for screening for activating compounds are also applicable to screening for enzyme inhibitors. For example, the method can be practiced using supports bearing a tether and compound, but lacking a tag identifying the compound, provided the compound is present in multiple copies per support and is subject to only partial release from the support leaving sufficient residual compound for direct release. As a further example, compounds representing the products of secondary metabolism, can be screened for inhibiting activity when produced by cells that express a tether as a cell surface marker. Cells producing compounds and displaying a tether from their outersurface are contacted with enzyme in a matrix in the same manner as described above. Compounds are secreted, or otherwise released from the cells, and a compound having inhibiting activity protects the tether of the cell from which it was released from enzymatic modification. Cells having unmodified tethers are isolated, cloned by limiting dilution, and propagated to express large amounts of compounds having inhibiting activity.

IV. Screening for Antagonists

The principles described above for screening for agonists of cellular receptors can be adapted to screen for antagonists. In one variation, complexes bearing compounds, tags and tethers are contacted with reporter cells with a receptor in the presence of a ligand to the receptor. The reporter cells contain a segment encoding a reporter molecule whose expression is coupled to signal transduction by the ligand through the receptor. In this situation, in cells proximate to complexes bearing antagonist compounds, the antagonist blocks signal transduction and modification of the tethers of complexes proximate to such cells does not occur. In other cells, proximate to complexes lacking antagonist compounds, the ligand causes signal transduction, the reporter molecule is expressed and released from the cells, and modifies the tethers of the complexes proximate to the cell. The result is a collection of complexes, some of which bear modified tethers and some unmodified tethers. Complexes bearing unmodified tethers are isolated, these being enriched for compounds having antagonist activity.

In a variation, the reporter cells have a DNA segment encoding a reporter molecule such that the reporter molecule is constitutively expressed and secreted. The reporter cells have a second DNA segment encoding an enzyme that is lethal to the cell whose expression is coupled to signal transduction through a cellular receptor by a ligand. Suitable lethal genes include the Bacillus amyloliquefaciens ribonuclease (Hartlet, *J. Mol. Biol.* 89 (1985)) and CLY mutants of the yeast PKC1 gene (Paravicini et al., *Mol. Cell. Biol.* 12, 4896–4905 (1992)). A library of complexes having compounds, tags and tethers is contacted with reporter cells in the presence of the ligand. In cells proximate to a complex bearing a compound that is an antagonist, the antagonist blocks signal transduction by the ligand through the receptor. Accordingly, the lethal gene is not expressed and the cell survives. The cell constitutively expresses the reporter molecule which is released from the cell and modifies the tether of the complex which bore the antagonist compound. Conversely, in other cells that are not proximate to an antagonist compound (usually the majority of cells), the ligand transduces a signal through the receptor causing expression of the lethal gene and death of the cell. Expression of the reporter molecule is thereby terminated. Accordingly, the level of reporter molecule surrounding complexes lacking antagonist compounds is low, and the tethers of such complexes remain largely unmodified. Separation of complexes bearing modified tethers enriches for complexes from which antagonizing compounds were released. The identity of such compounds can be decoded from the tags.

V. Analog Compounds

The compounds isolated by the above methods also serve as lead compounds for the development of analog compounds. The analogs should have a stabilized electronic configuration and molecular conformation that allows key functional groups to be presented to the receptor in substantially the same way as the lead compound. In particular, the analog compounds have spatial electronic properties which are comparable to the binding region, but can be smaller molecules than the lead compound, frequently having a molecular weight below about 2 kD and preferably below about 1 kD. Identification of analog compounds can be performed through use of techniques such as self-consistent field (SCF) analysis, configuration interaction (CI) analysis, and normal mode dynamics analysis. Computer programs for implementing these techniques are available. See Rein et al., *Computer-Assisted Modeling of Receptor-Ligand Interactions* (Alan Liss, New York, 1989).

VI. Pharmaceutical Compositions

Transducing compounds identified by the above methods or analogs are formulated for therapeutic use as pharmaceutical compositions. The compositions can also include, depending on the formulation desired, pharmaceutically-acceptable, usually sterile, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

From the foregoing, it should be apparent that many of the described methods have several general features which can be expressed concisely as follows. The methods entail the use of a complex comprising a compound under test, and a tether susceptible to modification to screen the compound for a desired activity, whereby the desired activity can be determined from the presence or absence of modification of the tether. In many uses, the complexes further comprise a tag recording at least one step in synthesis of the compound borne by the complex. After modification of tags, at least one step in the synthesis of a compound having the desired activity can be determined by decoding the tag. Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

decoding the tag of the at least one complex having the modified tether to identify at least one step in the synthesis of a compound having the desired property.

2. The method of claim 1, wherein the desired property is capacity to transduce a signal through a cellular receptor and the test compounds are screened by:

contacting the complexes with cells having a receptor and a DNA segment encoding a reporter molecule; whereby the tether of the compound of the at least one complex is modified by the compound transducing a signal through the receptor of a cell causing expression of the reporter molecule from the DNA segment, which

What is claimed is:

1. A method of screening compounds for a desired property, the method comprising:

providing a library of complexes, each complex comprising a compound under test, a tag recording at least one step in the synthesis of the compound, and a tether susceptible to modification by a reporter molecule produced in screening the test compounds, wherein at least one, but not all, of the complexes have a tether that has been modified by the reporter molecule, the modification indicating that the at least one complex bears a compound having the desired property;

separating the at least one complex having a modified tether from the library by virtue of the modified tether; and reporter molecule is released from the cell and modifies the tether of the at least one complex.

3. The method of claim 2, wherein each complex further comprises a support bearing the compound under test, the tag and the tether.

4. The method of claim 3, wherein the support is a bead.

5. The method of claim 3, wherein the support is at least two linked beads.

6. The method of claim 3, wherein the contacting step further comprises freeing the test compounds from the supports such that the at least one compound is free of its support in transducing the signal through the receptor of the cell.

7. The method of claim 6, wherein the test compounds are linked to the supports by a photocleavable linker and the test compounds are freed from the supports by exposure to radiation.

8. The method of claim 6, wherein first and second aliquots of each compound are linked to the supports by first and second linkers, whereby the first and second aliquots of compound can be separately freed from the supports on cleaving the first and second linkers.

9. The method of claim 6, wherein the freeing step is incomplete leaving the supports bearing residual amounts of the compounds.

10. The method of claim 3, wherein the tags are nucleic acids or inert hydrocarbons.

11. The method of claim 8, wherein the test compounds are selected from the group consisting of polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, thiazolidinones and imidizolidinones.

12. The method of claim 3, wherein the reporter molecule is operably linked to a signal sequence that directs the secretion of the reporter molecule from the cell.

13. The method of claim 12, wherein:
the reporter molecule is operably linked to a phospholipid anchoring sequence,
the reporter molecule is secreted from the cell, where it binds to phospholipid on the cell surface through the phospholipid anchoring sequence; and
the method further comprises treating the cells with a phospholipase to release the reporter molecule.

14. The method of claim 3, wherein the reporter molecule is released by lysis of the cells.

15. The method of claim 3, wherein the receptor is a cell surface receptor.

16. The method of claim 15, wherein the receptor is heterologous to the cells.

17. The method of claim 16, wherein the receptor is a G-protein coupled receptor, a cytokine receptor or a growth factor receptor.

18. The method of claim 3, wherein the reporter molecule is expressed from a fos promoter or a segment thereof effective to promote transcription, which promoter or segment is activated by the signal transduced through the receptor.

19. The method of claim 3, wherein the supports are contacted with the cells in a gel matrix.

20. The method of claim 6, wherein in the contacting step, the supports are contacted with the cells in wells of a plate, whereby after release from the cell, the reporter molecule is confined within the well containing the cell and can only modify the tethers of complexes within that well.

21. The method of claim 20, wherein first and second aliquots of the test compounds are linked to the supports by first and second linkers, and the method comprises at least two cycles of screening,
the first cycle comprising:
contacting the supports with the cells such that at least some wells each contain a plurality of supports,
freeing the first aliquots of test compounds from the supports, whereby in a well containing the at least one complex, the compound of the at least one complex transduces the signal through the receptor of a cell causing expression of the reporter molecule, which reporter molecule is released from the cell and modifies the tether of the at least one complex as well as the tethers of other compounds in the same well, and the second cycle comprising
isolating the supports having modified tethers and converting the modified tethers to unmodified tethers,
contacting the isolated supports having unmodified tethers with the cells in wells of a fresh plate whereby at least some wells each contain a single support,
freeing the second aliquots of the test compounds from the isolated supports having unmodified tethers, whereby the compound of the at least one complex transduces the signal through the receptor of a cell causing expression of the reporter molecule, which reporter molecule is released from the cell and modifies the tether of the at least one complex.

22. The method of claim 3, wherein the reporter molecule is protease and the tether has a site cleavable by the protease.

23. The method of claim 3, wherein the reporter molecule is BirA and the tether has a site susceptible to biotinylation by BirA.

24. The method of claim 3, wherein the cells further comprise a second segment encoding a second reporter molecule, and the reporter molecule induces expression of the second reporter molecule, whereby the second reporter molecule modifies the tether.

25. The method of claim 3, wherein the cells further comprises a second segment encoding a second reporter molecule, which is constitutively expressed, and the reporter molecule lyses the cell causing release of the second reporter molecule whereby the second reporter molecule modifies the tether.

26. The method of claim 3, wherein the cells in the contacting step further comprise a second DNA segment comprising a coding sequence for a second reporter molecule, which coding sequence is disrupted by an inactivating sequence flanked by sites recognized by the site-specific recombinase, and the reporter molecule is a site-specific recombinase whereby the the compound of the at least one complex causes expression of the site-specific recombinase, which excises the inactivating sequence from the coding sequence resulting in expression of the second reporter molecule, which is released from the cell and modifies the tether of the at least one complex from which the compound was released.

27. The method of claim 26, wherein the site-specific recombinase is cre and the sites recognized by the recombinase are loxP sites.

28. The method of claim 26, wherein the site-specific recombinase is Flp and the sites recognized by the recombinase are frt sites.

29. The method of claim 22, wherein the reporter molecule expressed from the DNA segment in the cells in the contacting step is tPA, the tether has a site cleaved by plasmin, and the method further comprises contacting the cells with plasminogen, whereby the tPA cleaves the plasminogen generating plasmin which modifies the tether.

30. The method of claim 3, wherein in the separating step, the support of the at least one complex having the modified tether is isolated from supports bearing unmodified tethers by screening with a labelled receptor having specific affinity for the modified tether.

31. The method of claim 3, wherein in the separating step, the support of the at least one complex bearing the modified tether is isolated from supports bearing unmodified tethers by screening with a labelled receptor having specific affinity for the unmodified tethers.

32. The method of claim 31, wherein the label is gold.

33. The method of claim 3, further comprising mixing the compound transducing the signal with a pharmaceutical carrier.

34. The method of claim 3, wherein at least $10^6$ compounds are provided.

35. The method of claim 3, wherein the test compounds are polymers and the tags identify each monomer component of the polymers.

36. The method of claim 3, wherein the at least one complex comprises a plurality of complexes collectively bearing a plurality of compounds which transduce the signal through the receptor of a plurality of cells, and the reporter molecule secreted by each of the plurality of cells modifies the tether of the support from which the compound transducing the signal in that cell was released.

37. The method of claim 3, wherein the cells used in the contacting step have a second DNA segment encoding a second reporter molecule, and the signal transduced through the receptor of the cell by the compound of the at least one complex causes expression of the reporter and second reporter molecules, whereby the second reporter molecule activates the reporter molecule and the activated reporter molecule modifies the tether.

38. The method of claim 3, wherein the cells used in the contacting step have a second receptor and a second DNA segment encoding a second reporter molecule, whereby (1) a compound under test, which has the capacity to transduce a signal through the receptor and the second receptor, transduces a signal through the receptor and the second receptor causing expression of the reporter molecule and the second reporter molecule, whereby the second reporter molecule inactivates the reporter molecule rendering it incapable of modifying the tether, (2) the compound of the at least one complex is a compound under test, which has the capacity to transduce a signal through the receptor but not through the second receptor, and transduces a signal through the receptor of the cell causing expression of the reporter molecule, which is released from the cell and modifies the tether of the support of the at least one complex from which the compound transducing the signal was released, thereby indicating that the compound has the capacity to transduce a signal through the receptor but not through the second receptor.

39. The method of claim 38, wherein the cells used in the contacting step comprise first and second cells, the first cells having the DNA segment encoding the reporter molecule and the second cells having the second DNA segment encoding the second reporter molecule, wherein the reporter and second reporter molecules are released from the first and second cells before the second reporter molecule inactivates the reporter molecule.

40. The method of claim 1, wherein the desired property is capacity to inhibit enzymatic modification of a substrate, and test compounds are screened by:

contacting the complexes with the enzyme and releasing the test compounds from the complexes within a matrix that retains a released compound in proximity to the complex from which it was released, whereby the enzyme modifies the tether of complexes from which compounds lacking enzyme inhibiting activity were released without modifying the tether of at least one complex from which a compound having enzyme inhibiting activity was released due to protection of the tether by the compound.

41. The method of claim 40, wherein the compounds are released from the complexes after contacting the complexes with the enzyme.

42. The method of claim 40, wherein the enzyme is a protease, phosphatase, kinase, glycosylase, or polymerase.

43. The method of claim 42, wherein the enzyme is a protease and the tether is a protein containing a site cleavable by the protease.

44. The method of claim 3, wherein the cells further comprise a second segment encoding a second reporter molecule, which is expressed from the second segment, and the reporter molecule modifies the second reporter molecule, whereby the modified second reporter molecule modifies the tether.

* * * * *